(12) United States Patent
Juvinall et al.

(10) Patent No.: US 8,941,825 B2
(45) Date of Patent: Jan. 27, 2015

(54) CONTAINER INSPECTION

(71) Applicant: Owens-Brockway Glass Container Inc., Perrysburg, OH (US)

(72) Inventors: John W. Juvinall, Ottawa Lake, MI (US); James A. Ringlien, Maumee, OH (US)

(*) Notice: Subject to any disclaimer, the term of this patent is extended or adjusted under 35 U.S.C. 154(b) by 146 days.

(21) Appl. No.: 13/834,653

(22) Filed: Mar. 15, 2013

(65) Prior Publication Data

US 2014/0268123 A1    Sep. 18, 2014

(51) Int. Cl.
*G01N 21/00*    (2006.01)
*G01N 21/90*    (2006.01)

(52) U.S. Cl.
CPC .......... *G01N 21/9081* (2013.01); *G01N 21/90* (2013.01); *G01N 21/9054* (2013.01)
USPC ..................................... 356/239.4; 356/240.1

(58) Field of Classification Search
USPC .......... 356/239.4, 240.1, 239.1, 241.1, 237.1, 356/428; 250/223 B, 559.22–559.24, 250/559.28, 559.37, 559.38; 209/526
See application file for complete search history.

(56) References Cited

U.S. PATENT DOCUMENTS

| | | |
|---|---|---|
| 3,030,516 A | 4/1962 | Seavey |
| 3,069,553 A | 12/1962 | Zoltanski |
| 3,262,561 A | 7/1966 | Sorbie |
| 3,287,564 A | 11/1966 | Gore et al. |
| 3,302,786 A | 2/1967 | Conrad |
| 4,213,702 A | 7/1980 | Bryant et al. |
| 4,411,522 A | 10/1983 | O'Connor et al. |
| 4,491,728 A | 1/1985 | Fischer |
| 4,874,940 A | 10/1989 | McMeekin et al. |
| 5,020,908 A | 6/1991 | Hermann |
| 5,200,801 A | 4/1993 | Juvinall et al. |
| 5,637,864 A | 6/1997 | Nicks et al. |
| 5,825,476 A | 10/1998 | Abitol et al. |
| 5,895,911 A | 4/1999 | Giometti et al. |
| 5,896,195 A | 4/1999 | Juvinall et al. |
| 5,900,945 A | 5/1999 | Hinata et al. |
| 6,025,909 A | 2/2000 | Juvinall et al. |
| 6,031,221 A | 2/2000 | Furnas |
| 6,104,482 A | 8/2000 | Brower et al. |
| 6,175,107 B1 | 1/2001 | Juvinall |
| 6,211,952 B1 | 4/2001 | Weiland et al. |

(Continued)

FOREIGN PATENT DOCUMENTS

| | | |
|---|---|---|
| DE | 38 15539 A1 | 11/1989 |
| EP | 0 061 021 A2 | 9/1982 |

(Continued)

OTHER PUBLICATIONS

PCT Search Report and Written Opinion, Int. Serial No. PCT/US2014/020981, Int. Filing Date: Mar. 6, 2014, Applicant: Owens-Brockway Glass Container Inc., Mail Date: Jul. 2, 2014.

*Primary Examiner* — Tri T Ton

(57) ABSTRACT

Method and apparatus for detecting commercial variations in at least a portion of an at least partially transparent container. A light pattern in an angular domain is established from signals generated by a plurality of light sensors, wherein a point in the light pattern is generated by a signal from a corresponding portion of the light sensors and represents a light intensity corresponding to a particular reflection angle of a light ray reflected off the container. Different types of commercial variations in the container can be differentiated by analyzing the light pattern in the angular domain.

47 Claims, 16 Drawing Sheets

(56) References Cited

U.S. PATENT DOCUMENTS

| | | |
|---|---|---|
| 6,275,287 B1 | 8/2001 | Watanabe |
| 6,480,280 B1 | 11/2002 | Hinata |
| 6,556,706 B1 | 4/2003 | Geng |
| 6,618,495 B1 | 9/2003 | Furnas |
| 7,060,999 B2 | 6/2006 | Juvinall |
| 7,329,855 B2 | 2/2008 | Katayama et al. |
| 7,330,251 B2 | 2/2008 | Katayama et al. |
| 7,414,716 B2 | 8/2008 | Sones et al. |
| 7,541,572 B2 | 6/2009 | Novini et al. |
| 7,697,132 B2 | 4/2010 | Sones et al. |
| 7,929,129 B2 | 4/2011 | Berg et al. |
| 8,135,206 B2 | 3/2012 | Sones et al. |
| 8,164,746 B2 | 4/2012 | Colle |
| 2011/0134317 A1 | 6/2011 | Wang |
| 2011/0191073 A1 | 8/2011 | Kim et al. |
| 2011/0311132 A1 | 12/2011 | Meimoun |

FOREIGN PATENT DOCUMENTS

| | | |
|---|---|---|
| EP | 0328 374 A3 | 8/1989 |
| EP | 0338446 | 10/1989 |
| EP | 0763727 | 3/1997 |
| EP | 1106993 | 6/2001 |
| FR | 2432342 | 2/1980 |
| JP | 54 156594 A | 12/1979 |
| JP | 57 63438 A | 4/1982 |

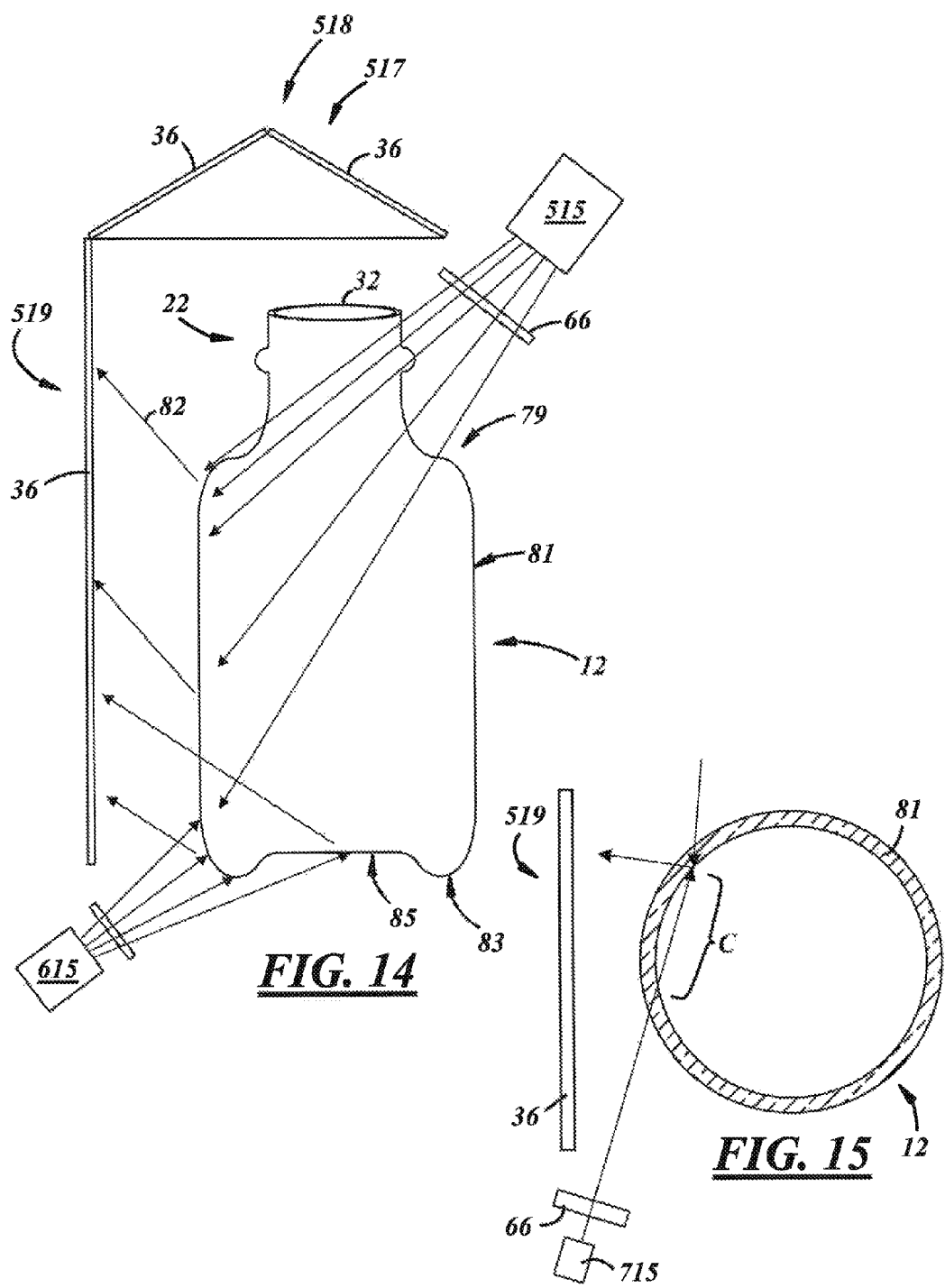

Vertical Check

Horizontal Check

Nearly Vertical Check

Nearly Horizontal Check

Nearly Vertical Check

Top View of tilted Vertical Check

Top View of straight Vertical Check

US 8,941,825 B2

CONTAINER INSPECTION

The present disclosure relates generally to inspection of containers and more particularly to an apparatus and method for detecting commercial variations in a container.

BACKGROUND AND SUMMARY OF THE DISCLOSURE

In the manufacture of containers such as glass containers, certain features, properties or dimensions may vary from one container to another. Some of the variations may be within commercially acceptable standards or thresholds and other variations may be outside of such standards or thresholds. It is known to inspect containers, such as glass containers, for commercial variations that are not acceptable to the manufacturer. Some variations include "checks" which are cracks within the container. Checks are sometimes broken down into two categories including "horizontal checks" and "vertical checks". Horizontal checks are generally perpendicular to a longitudinal axis of the container, and thus "horizontal" when the container is in upright orientation. Vertical checks are checks that are generally parallel to the axis of the container and thus in "vertical" orientation when the container is upright. "Blisters", unacceptable seams from the molding process, and other variations also may be detected and compared against suitable thresholds.

The present disclosure embodies a number of aspects that can be implemented separately from or in combination with each other.

In one implementation, an apparatus is provided for detecting commercial variations in at least a portion of an at least partially transparent container having an open mouth. At least one light source directs light toward a region of interest of the container such that the light reflects off the region of interest as reflected light rays extending at different reflection angles. A plurality of light sensors receive the reflected light rays, wherein parallel reflected light rays travel to common portions of the light sensors and non-parallel light rays travel to different portions of the light sensors, wherein the light sensors are used to establish a light pattern in an angular domain such that a point in the light pattern is generated by a signal from a corresponding portion of the light sensors and represents a light intensity corresponding to a particular reflection angle. A processor receives signals from the light sensors and differentiate between different types of commercial variations in the container by analyzing the light pattern in the angular domain.

According to another implementation, a method is provided for detecting commercial variations in at least a portion of an at least partially transparent container. The method includes the following steps:

directing light toward a region of interest of the container from at least one light source such that the light reflects off the region of interest as reflected light rays extending at different reflection angles;

receiving the reflected light rays with a plurality of light sensors, wherein parallel reflected light rays travel to common portions of the light sensors and non-parallel light rays travel to different portions of the light sensors;

establishing a light pattern in an angular domain from signals generated by the light sensors, wherein a point in the light pattern is generated by a signal from a corresponding portion of the light sensors and represents a light intensity corresponding to a particular reflection angle; and differentiating between different types of commercial variations in the container by analyzing the light pattern in the angular domain.

BRIEF DESCRIPTION OF THE DRAWINGS

The disclosure, together with additional objects, features, advantages and aspects thereof, will best be understood from the following description, the appended claims and the accompanying drawings, in which:

FIGS. 14 and 15 are schematic views of a further embodiment of an apparatus that may be used during inspection of a container to detect commercial variations within the container;

DETAILED DESCRIPTION OF PREFERRED EMBODIMENTS

Figure 1:
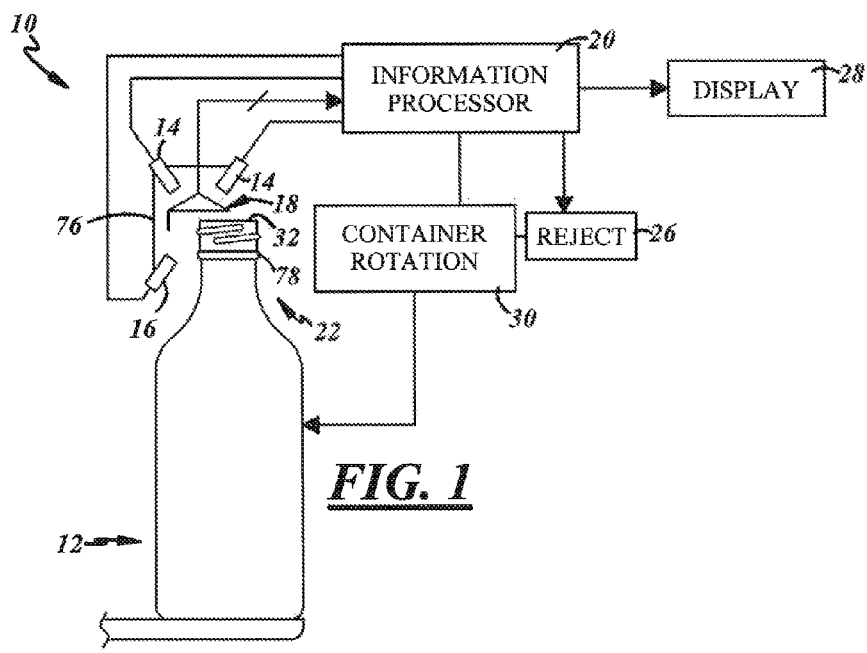
FIG. 1 is a schematic view of an apparatus that may be used during inspection of a container to detect commercial variations within the container.

Referring in more detail to the drawings, FIG. 1 illustrates an apparatus 10 for detection of unacceptable commercial variations during inspection of a container 12, which may be formed of a transparent or partially transparent material, for example, glass. In general, the apparatus 10 may include a plurality of light sources 14, 16, a light receiver 18, and an information, data, and/or signal processor 20. The light sources 14, 16 direct light onto at least a portion of the container 12, and in one particular implementation, onto a neck finish 22 of the container 12 although other regions of the container 12 may be inspected. Commercial variations within the container neck finish 22 reflect or refract the light into or onto the light receiver 18 which may include a plurality of sensors 24 capable of detecting the reflected or refracted light. As used herein, the term "reflect" also includes light that may be reflected off a commercial variation but refracted through the container material. Likewise, the term "onto" includes light impinging on an external surface of a container and also therethrough.

The light directed onto the container 12 by the light sources 14, 16 may include an elongate light beam that may extend along a plane established by the longitudinal axis of the container 12. The light beam may be produced via a ray in the shape of a line-shaped beam, or via a ray in the shape of a point-shaped beam that is scanned up and down along a desired length of a line, or the like. In the former implementation, the light sources 14, 16 may include laser line generators, which each direct a line-shaped light beam of a predetermined line length and width onto the neck finish 22 of the container 12. In the latter implementation, the light sources 14, 16 may include laser scanners, which each direct a discrete point-shaped light beam of a predetermined point size onto the neck finish 22 of the container 12 and rapidly scan the light beam up and down, side to side, or the like, to generate a luminous line of inspection on the container 12.

The processor 20 is coupled to the light receiver 18 and its sensors 24 and receives signals from the sensors 24 that are indicative of the light detected by the sensors 24. From these signals, the processor 20 may determine whether a commercial variation is within or outside of acceptable limits or thresholds, or does or does not match a reject pattern or exceed a threshold because of, for example, the angular reflections pattern's size, location, and/or shape. As will be described in further detail below, different thresholds may be used after a determination is made as to the commercial variation type, for example, check, blister, or the like. The processor 20 may itself send a signal to a reject mechanism 26 to remove from further processing a container in which unacceptable commercial variations have been detected. The processor 20 may also provide an output to a display 28 for monitoring by plant personnel, or to a process control computer to help control an upstream container manufacturing process as a function of the output data from this system.

In one example, the processor 20 may be part of a glass container inspection computer including memory coupled to the processor 20, and one or more interfaces coupled to the processor 20 and coupled to one or more input devices (e.g. image sensors, position sensors, user interfaces, etc.) and/or one or more output devices (e.g. light sources, material handlers, displays, etc). Of course, the computer further may include any ancillary devices, for example, clocks, internal power supplies, and the like (not shown). The processor 20 may process data and execute instructions that provide at least some of the functionality for the presently disclosed apparatus. As used herein, the term "instructions" may include, for example, control logic, computer software and/or firmware, programmable instructions, or other suitable instructions. The memory may include any computer readable medium or media configured to provide at least temporary storage of at least some data, data structures, an operating system, application programs, program modules or data, and/or other computer software or computer-readable instructions that provide at least some of the functionality of the presently disclosed apparatus and that may be executed by the processor. The data, instructions, and the like may be stored, for example, as look-up tables, formulas, algorithms, maps, models, and/or any other suitable format.

Figure 2:
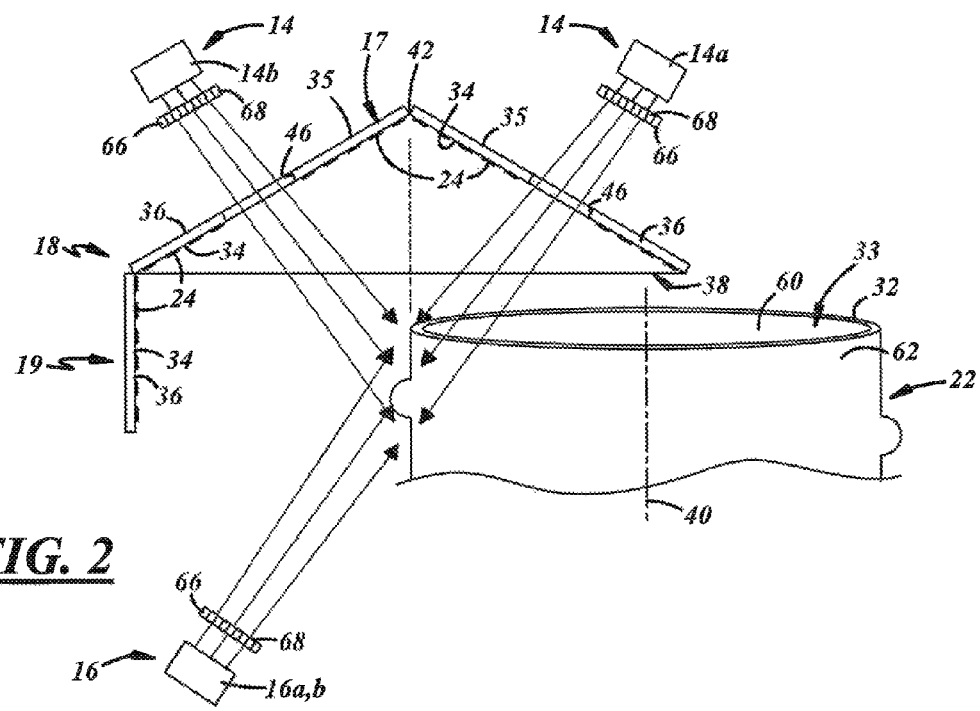
FIG. 2 is an enlarged, fragmentary, schematic view showing a portion of the apparatus of FIG. 1 and a container neck finish.

The container 12 may be moved by a material handler 30 at an inspection station while the light sources 14, 16 are energized to permit inspection of at least a portion of the container neck finish 22 and its finish end 32 which defines an open mouth 33 (FIG. 2). The material handler 30 can be of any suitable type. Processor 20 can monitor receiver 18 and material handler 30 at increments of container movement (rotation and/or translation), or at selected time increments while the container 12 is rotated and/or translated at constant or varying velocity.

As best shown in FIGS. 1-5, the light receiver 18 may be generally dome shaped providing a generally continuous, concave inside surface 34 (FIGS. 2 and 5) located and shaped to capture as many reflections or refracted light from the container 12 as desired or possible. The term "dome" is used in a broad sense to include partial polyhedrons, cones, pyramids, partial spheres, portions of a geodesic dome, as well as non-uniform shapes which may be used to capture reflected or refracted light. The light receiver 18 also includes an exterior surface 35 disposed opposite of the inside surface 34. The light receiver 18 may be formed of sections of regular or irregular polygons. The inside surface 34 of the light receiver 18 may be contoured to receive light reflected or refracted at a wide range of angles, which allows detection of checks disposed at angles that vary orthogonally from the line of light directed onto the container 12 by the light sources 14, 16. In other words, the apparatus 10 may be used to detect purely horizontal or vertical checks, or checks disposed at any angle therebetween.

The light receiver 18 may be formed as close as possible to a complete enclosure with a first relief 38 through which reflected or refracted light may pass, to enable the dome to receive light at a greater range of angles. In view of this, a wide range of angles of reflected or refracted light may be detected and analyzed without the use of lenses. However, lenses may be used to block secondary reflections, as will be described herein below. The relief 38 may also permit containers 12 being inspected to be moved into and out of position relative to the light receiver 18, preferably without having to move the light receiver 18.

As shown in FIGS. 1 and 2, the light receiver 18 may be disposed adjacent the container 12, for example, generally above the container neck finish 22 and outside of the path of the container 12 to allow containers to enter and exit the inspection station. In one implementation, the light receiver 18 includes a dome 17 disposed adjacently above the container 12 and an extension 19 depending downwardly from a portion of the dome 17 and disposed adjacently alongside of the container 12. The dome 17 may be laterally offset from a longitudinal axis 40 of the container 12 about which the container 12 may be rotated by the material handler 30 during inspection.

Figure 3:
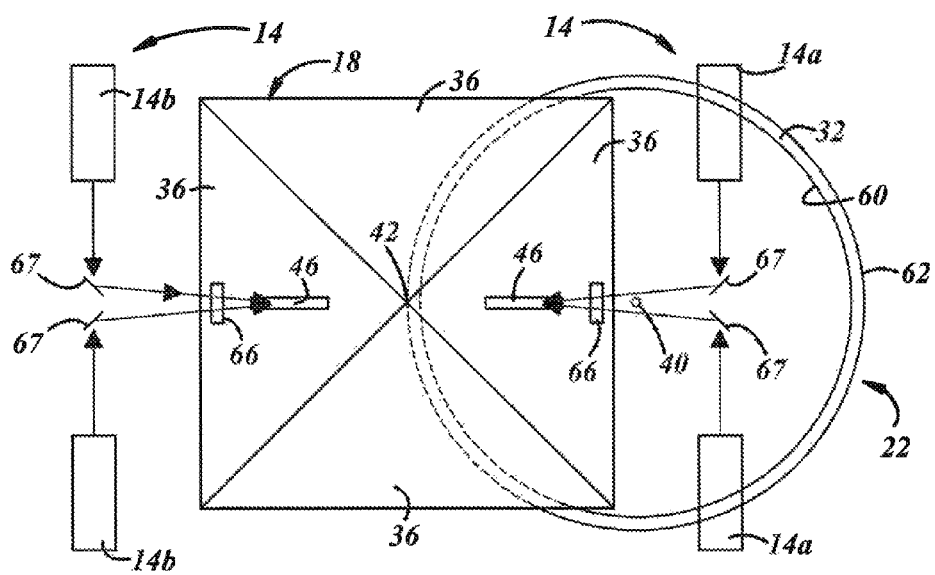
FIG. 3 is a schematic plan view of the apparatus of FIG. 1 showing two pairs of first light sources with second light sources not shown.
Figure 4:
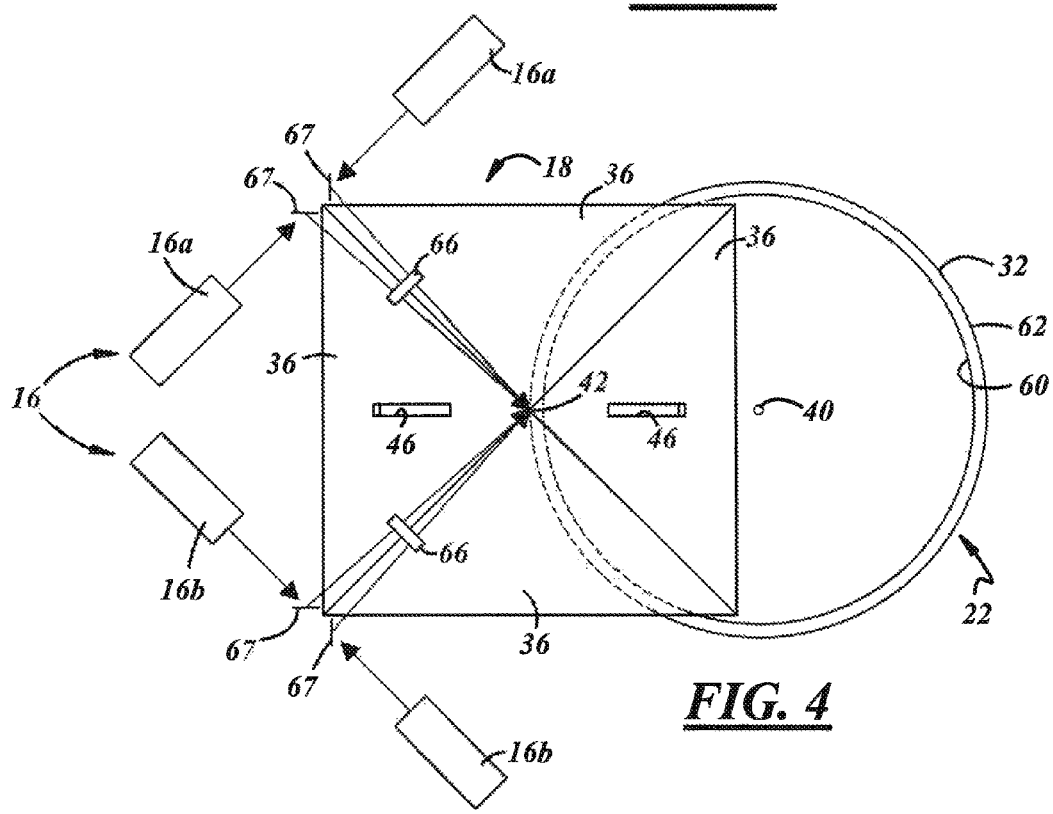
FIG. 4 is a schematic plan view of the apparatus of FIG. 1 showing two pairs of second light sources with the first light sources not shown.

As shown in FIGS. 2 through 4, an apex or center 42 of the dome 17 may be aligned with a peripheral edge of the container neck finish 22 being inspected. Doing so permits consistent operation of the inspection apparatus 10 with containers 12 having mouths of different diameter. By positioning the dome 17 so that it is centered over a peripheral edge of the finish 22, and by aligning the light sources to a region at the peripheral edge of the neck finish 22, the positions of the individual elements in the assembly (e.g. the dome and light sources) can be fixed so that the entire assembly can be moved when containers with a different diameter finish are to be inspected. To inspect a container with a different diameter finish, the assembly can simply be moved (manually via a scale, or automatically using servos or the like) to align the assembly with the peripheral edge of the finish of the new containers. In this manner, any diameter container can be accommodated, at least within the limits of adjustment of the dome 17 and light sources 14, 16. On the other hand, if the dome 17 were axially centered over a central axis of the container 12, then the dome 17 would have to be sized to capture reflected or refracted light from even the largest mouthed containers to be inspected.

Figure 5:
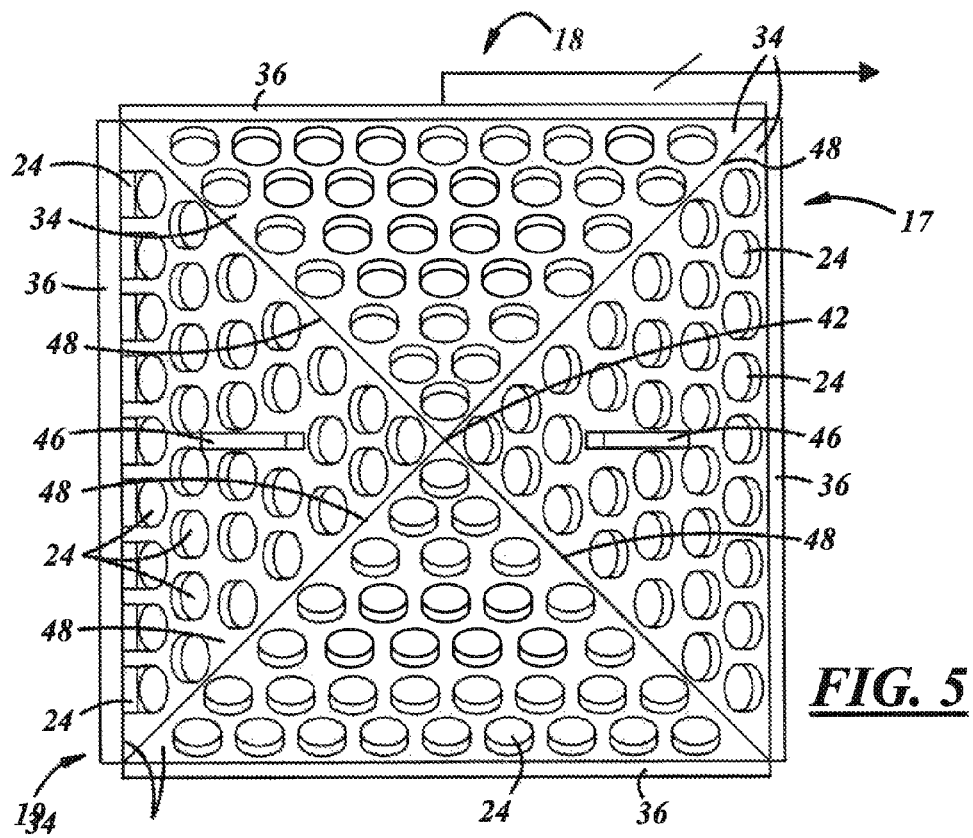
FIG. 5 is a schematic view of the inside of one implementation of a light receiver of the apparatus of FIG. 1.

As shown in FIG. 5, the inside surface 34 of the dome 17 may be covered with one or more light sensors 24, which may be referred to as photocells, light detectors, or the like. The sensors 24 may be large photosensitive layers or chips, or arrays of smaller sensors. For example, one array of smaller sensors could include a three-by-three array of nine smaller sensors. In the light receiver 18 of FIG. 5, the dome 17 may be pyramid shaped and may include four triangular facets or panels 36. The light receiver 18 may also include one or more depending surfaces or panels 36 which may extend beneath the vertical height of the portion of the container being inspected and may be curved or disposed at different angles to receive light reflected or refracted at lower angles than the rest of the dome 17.

Each panel 36 may include a plurality of light sensors 24 which may be uniformly spaced apart. Each panel 36 may include, for example, 16 to 66 light sensors 24 that may nearly completely cover the inside surface of each panel 36. The light collected from the sensors 24 are converted to digital signals in any suitable manner. For example, the sensors 24 may be coupled to amplifiers, multiplexer(s), and analog-to-digital (A/D) converters, and other appropriate signal conditioners, and are adapted to provide a signal to the processor 20 that is indicative of the position/location, pattern and/or intensity of light detected. The sensors 24 may be silicon, germanium, CdS, commercially available CCD or CMOS type sensors, or other photosensitive devices or materials. To reduce the number of signals and/or the number of amplifiers and related signal conditioners needed, the sensors 24 may be coupled in groups. In one illustrative implementation, the sensors 24 may be coupled in sixteen parallel groups per panel 36 or section of the light receiver 18, and each group from each panel 36 may be connected to one amplifier and one A/D converter. An additional component, such as a Field Programmable Gate Array (FPGA) may be used to receive the signals from the plurality of panels 36 and serialize the signals for transmission to the processor 20 for subsequent processing.

With reference to FIGS. 2 through 5, the light receiver 18 also may include one or more second reliefs 46 extending between the interior and exterior surfaces 34, 35 of the light receiver 18 and through which light from one or more light sources 14, 16 may be directed onto the containers 12 being inspected. As shown in FIG. 2, the second reliefs 46 may be located between one or more of the light sources 14, 16 and the first relief 38. As shown, the reliefs 46 may be slits; having a length greater than their width.

With reference to FIG. 5, to receive and detect as much reflected or refracted light as possible, it may be desirable to cover as much of the inside surfaces 34 of the light receiver 18 with sensors 24 or sensor material as possible. In a pyramidal dome 17 with panels 36 that are engaged along their edges, there may be gaps 48 left along the junction between adjacent panels. The gaps 48 can be reduced or eliminated by, for example, overlapping the panels 36.

The processor 20 may be coupled to the light sources 14, 16 and to the sensors 24 to energize the light sources 14, 16 and to receive signals from the sensors 24 to detect commercial variations in the container 12 as a function of at least one pattern of reflection angles of light incident on one or more of the sensors 24 when the light sources 14, 16 are energized. More specifically, the commercial variations may be detected as a function of a pattern of intensities of light rays reflected off the container 12 at different reflection angles. The processor 20 may be responsive to an ambient light level when the light sources 14, 16 are not energized and may remove the ambient light level from signals from the sensors 24.

The light sources 14, 16 may direct line of lights onto the container 12, and the processor may sum signals from the light sensors 24 as the intensity of light detected by the light sensors 24, in order to produce a spatial domain image in a spatial domain image plane and having a vertical axis corresponding to each point along the directed line of light and a horizontal axis corresponding to movement of the container 12. Also, the cell array may generate a two-dimensional reflection angle image or angular domain image corresponding to each point in the spatial domain image.

This implementation will produce multiple two-dimensional spatial domain images of the unwrapped container finish that are created by the processor summing the data in the angular domain images to create each point in the spatial domain images. Each spatial domain image is produced by light hitting the container from different directions. For each point in each spatial domain image, there will be a two dimensional pattern of the angles of light that leave a corresponding point or portion of the container as reflected off the container from the designated light source. This will give both spatial and angular information about every point, for example, in the container neck finish.

This data can be reduced by including zones in the spatial domain images to produce reflected or refracted light pattern images. These pattern images can be further reduced by association with the different inspection channel information. Further, any number of zones can be added without adding additional light sources. Each zone can have different sensitivities applied to it similar to use of a partial transmission on a LCD mask.

In operation, and referring to FIGS. 1 and 2, the light sources 14, 16 direct light on the container neck finish 22. The light sources 14, 16 preferably direct light onto the container neck finish 22 from a plurality of different locations to reduce the possibility that an unacceptable commercial variation does not reflect or refract light toward the dome 18. The light sources 14, 16 may include any suitable light emitter such as a laser, focused LED, incandescent light, fiber optic transmitter, or the like.

One or more first light sources 14 (e.g. lasers) may be used primarily to detect horizontal checks. As used herein, the terminology "horizontal checks" includes checks that are disposed at an angle between 45 and 90 degrees with respect to a longitudinal axis of the container. These horizontal check detecting light sources 14 illuminate the container neck finish 22 along or parallel to a diameter and may be disposed above the container neck finish 22 to shine downwardly on the container neck finish 22.

In one implementation as shown in FIGS. 2 and 3, at least one light source 14a is directed onto an interior surface 60 of the container neck finish 22, and at least one light source 14b is directed onto an exterior surface 62 of the container neck finish 22. The light from each light source 14a, 14b may be directed through one or more second reliefs 46 in the dome 18, the first relief 38 and onto the containers 12 being inspected. The light from the light sources 14a, 14b may be directed along a direction that is generally diametrically across, or along a diameter of, the container neck finish 22. The light sources 14a, 14b may be disposed at an angle greater than 0 degrees with respect to the longitudinal axis 40 of the neck finish 22 such that light from the light sources 14a, 14b is directed at an angle greater than 0 degrees to the axis 40.

As shown, two light sources 14a illuminate the interior surface 60 and two light sources 14b illuminate the exterior surface 62 of the container neck finish 22. The light sources 14a directed onto the interior surface 60 may each provide light directed at different vertical portions of the neck finish 22, which may be adjacent or overlapping portions, to facilitate determining the height or vertical location of a check in the neck finish 22 (such as when a check reflects light provided from one light source but not the other). The same may be true of the light sources 14b which direct light onto the exterior surface 62 of the container neck finish 22. Similar results could be achieved with a single light source and a mask or mirror movable to vary the location of the container illuminated by the light source in different cycles. In applications where speed of inspection is important, cycling multiple light sources may provide better results rather than physically moving a mask or other component. Each light source 14a may direct light onto generally the same radial location of the container neck finish 22, and that radial location preferably is aligned with the center of the dome, as shown in FIG. 2.

As shown in FIGS. 2 and 3, the emitted light from the light sources 14a, 14b may be directed through one or more mask (s) 66 by way of a mirror 67 (FIGS. 3 and 4) or directly from the light sources 14a, 14b. The masks 66 may be Liquid Crystal Devices (LCDs) coupled to the processor 20 for selectively controlling the pattern and intensity of light directed from the light sources 14a, 14b over the associated surface portion of the container neck finish. As shown in FIG. 2, each mask 66 may be comprised of a plurality of segments 68 with the transmission of each segment 68 capable of being controlled to permit control of light transmitted therethrough. For example, if a segment 68 were set to 0% transmission, the light would not pass through that segment, 50% transmission would permit half the emitted light through, and 100% transmission would permit essentially all of the emitted light at that segment through. While LCD masks are noted above, any mechanically or electronically adjustable mask may be utilized.

Referring to FIGS. 1 and 2, one or more second light sources 16 (e.g. lasers) also may be used primarily to detect vertical checks. As used herein, the terminology "vertical checks" includes checks that are disposed at an angle between 0 and 45 degrees with respect to a longitudinal axis of the container. These vertical check detecting light sources 16 may be mounted outside the container and preferably are oriented below the container neck finish 22 so that the emitted light is directed upwardly toward the container neck finish 22 at an acute included angle to the axis 40 of the container and reflected or refracted light is directed upwardly and toward the light receiver 18. That is, at least one second light source may direct light onto a surface of a container from a position wherein the portion of the container onto which light is directed is between the light receiver and the second light source.

In one implementation, as shown in FIG. 4, a plurality of second light sources 16 may be laterally spaced apart so that emitted light is directed onto the exterior surface 62 of the container neck finish 22 from at least two different directions. As shown, two light sources 16a illuminate the container neck finish 22 from a first direction, and two light sources 16b illuminate the container neck finish 22 from a second direction offset from the first direction. In the implementation shown in FIG. 4, the emitted light from the first pair of light sources 16a is offset from the emitted light from the second pair of light sources 16b by about 90 degrees. The light from the light sources 16a, 16b may be directed along a direction that is generally diametrically across, or along a diameter of, the container neck finish 22. The light sources 16a, 16b may be disposed at an angle greater than 0 degrees with respect to the longitudinal axis 40 of the neck finish 22 such that light from the light sources 16a, 16b is directed at an angle greater than 0 degrees to the axis 40. Of course, other arrangements with different angles and orientations may be used.

In the laser-line generator implementation of the light sources 14, 16, the location of a commercial variation is determined according to which portion of the LCD mask is transmitting. In the laser scanner implementation of the light sources 14, 16, the phase of the laser scan when a commercial variation is detected would give the location of the laser on the container and therefore the location vertically on the container of the commercial variation.

With general reference to FIGS. 2 through 4, providing light onto the container neck finish 22 from different locations and directions may facilitate detection of more checks in that some checks may not or refract light into the light receiver 18 when illuminated by light from one particular location and/or direction, but may reflect or refract light into the light source from another location and/or direction. The light sources 16 in each pair 16a, 16b may emit light onto different vertical portions of the neck finish 22 to facilitate determining the height or vertical location of a check in the neck finish (such as when a check reflects light provided from one light source but not the other). As noted with regard to the horizontal check light sources 14, a mirror 67 and/or mask 66 may be used to vary the location, pattern and/or intensity of the container 12 illuminated by a single light source. Each light source 16 may direct light onto generally the same radial and circumferential location of the container neck finish 22, and that location may be aligned with the center of the dome 17, if desired and as shown in FIG. 4, and may be the same location along the container neck finish 22 at which the horizontal check light sources 14 are directed, as generally shown in FIG. 2.

In some applications, a single light source 16 may provide sufficient detection of checks at various angles, and hence, the cost and complexity of multiple light sources could be avoided. The light sources 16a, 16b provide information about the height of a check to allow for different thresholds and to provide process control information. The pair of light sources 16a, 16b would not be required if a scanning laser was used instead.

In the presently described embodiment, however, eight light sources 14, 16 may be provided in four groups of two.

Each light source 14, 16 and the light receiver 18 may be fixed in position relative to each other, such as by being commonly supported on a head plate or frame 76 (FIG. 1) at or adjacent to an inspection station. In this way, the light sources 14, 16 and light receiver 18 can be moved as a single unit relative to containers 12 to be inspected. This may avoid the need to individually adjust and calibrate each component as containers 12 of different sizes or shapes are presented for inspection. Instead, the apex of the dome 17 can simply be aligned with a peripheral edge of the container neck finish 22 and disposed a desired distance above the container neck finish 22 to achieve consistent positions of the light receiver 18 relative to the container neck finish 22, and the light sources 14, 16 relative to the container 12 and the light receiver 18. In this manner, the system 10 may be readily adapted to inspect containers 12 of different shapes and sizes, and the downtime to switch from one container type to another is reduced.

Preferably, only one light source 14, 16 is energized at a time so that the container neck finish 22 is illuminated by only one light source at a time to avoid interference in the reflected or refracted light signals. Where multiple light sources 14, 16 are used, the light sources 14, 16 may be sequentially energized to sequentially direct a light source light line onto the container neck finish 22. Because only one light source 14, 16 is providing light at a time, light reflected or refracted into the light receiver 18 can be attributed to light from a particular light source.

Further, the light sources 14, 16 may be rapidly pulsed as the container 12 is rotated so that the entire circumference of the neck finish 22 is illuminated by at least one light source, and where more than one light source is used, the entire circumference may be illuminated by each light source.

For each increment in the scan of each light source, the light receiver 18 collects the light that impinges on the sensors thereof to produce an angular domain image of the distribution of the collected light where the location of each point in the angular domain image represents the angle of light leaving the container. The intensity of the light at each point in the angular domain image corresponds to the intensity of the light at or of the particular reflection angle. The sum of all of the data in the angular domain image is equal to the intensity of one point in a spatial image which will be described in detail further herein below.

The lasers may be modulated alternately such that images are obtained representing light from the lasers separately. A baseline image also may be taken at some point when the lasers are off, to represent an ambient light level that can be subtracted from each image taken with a laser on. One image per laser can be taken for each increment of the scan.

In one form, and referring to FIGS. 1 and 2, unacceptable commercial variations such as checks in the container neck finish 22 are detected as a function of the intensity of light detected by selected sensors 24 in the light source. As the container 12 is rotated and the light sources are energized one at a time, all of the sensors 24 in the light receiver 18 may be activated (that is, their output at that time may be examined, sampled or recorded) and the intensity of light detected by the sensors 24 recorded. Alternatively, only certain groups of sensors 24 could be activated for certain light sources 14, 16 (and hence, other sensors would be turned off, that is, their output would not be used or examined at that time) to, for example, ignore reflections caused by a thread 72 or bead 78 on the container 12. Light from threads 72 and beads 78 (FIG. 1) can otherwise be accounted for in the processing of the signals from the light sensors.

In that regard, certain groups of sensors 24 may be analyzed, and perhaps different groups for different light sources, to determine if an unacceptable commercial variation exists. The actively processed sensor groups for a given light source (which may be all or fewer than all groups) may define a channel, with a separate signal generated by the channel for each light source. Each group may provide a group signal to the processor 20 that is representative of the intensity of light detected by that group of light sensors. In addition to, or instead of, filtering out reflections caused by threads 72 and other intended container features, the masks 66, through which the light source lines may be emitted can mask the light to reduce or eliminate illumination of thread ends and the like which may cause reflections into the light receiver 18 but are not indicative of an unacceptable commercial variation.

In one implementation, although not necessarily preferred, detection may be carried out offline. In this implementation, reflected and/or refracted light patterns (location, intensity, size, orientation) may be imaged and stored. The stored light patterns may be analyzed or used as a reference against which light patterns acquired during subsequent container inspections can be compared. In this way, characteristics of reflected and/or refracted light in addition to intensity (e.g., its orientation or angle) can be analyzed. A wide range of light patterns may be cataloged or otherwise stored to establish a wide range of acceptable and/or unacceptable commercial variation reflection and/or refraction patterns for a given container size and shape. Then, light patterns captured during actual container inspections can be compared to the stored light patterns to determine if the light pattern captured during inspection is representative of a light pattern generated by an unacceptable commercial variation. This system may also permit identification of the type of unacceptable commercial variation (e.g. check or blister) as well as its location on the container neck finish. Lenses may be used in this implementation to focus the reflected or refracted light onto an imaging sensor or other light receiver and detector.

In another implementation, detection may be carried out in real-time. In this implementation, the intensity of the light detected in a channel may be compared to a threshold value for that channel to determine if an unacceptable commercial variation is present in the container neck finish. Also, container seams, beads and threads could also be checked against thresholds set for their size, shape, light angle pattern and/or location to determine if these normal container features are within acceptable limits.

Different thresholds can be set for different channels. One reason for doing this is that the light emitted by some light sources may cause reflections into the light receiver 18 from things other than container features, like adjacent machinery and the like. The light levels caused by reflections from things other than commercial variations may be filtered out or ignored by setting a higher light intensity threshold for a given channel. In an ideal setting, no light would be reflected onto the sensors 24 in the absence of an unacceptable commercial variation. However, in practice, reflections may occur off acceptable commercial variations, adjacent machinery or other components and so a threshold intensity value may be used to filter out or ignore such false reflections or noise when analyzing the generated signals.

Such undesired reflections can be reduced by blocking, to the extent possible, the emitted light source light after it passes through the container to prevent it from reflecting off other parts of the container, or the inspection machine, or other items. If collimators are used (as described in detail herein below), then they may eliminate the need to raise the thresholds due to the secondary reflections of the light source. Then, the signal will only be from the variation on the container being inspected. The thresholds can then be set to a level to distinguish acceptable commercial variations from unacceptable commercial variations The thresholds may vary for containers of different size and shape which may cause different reflections. The thresholds may be set by comparison of signals generated by inspection of known commercially acceptable and known commercially unacceptable test containers to provide a collection or database of signals from which signals from a wide range of unacceptable commercial variations can be determined to facilitate setting appropriate thresholds. Filter time constants can be different for horizontal checks, which tend to have lower frequencies, than for vertical checks, which tend to have higher frequencies.

With consistent placement of the light receiver 18 and light sources 14, 16 with respect to each other and to containers 12 being inspected, such as by fixing the position of the light sources 14, 16 relative to the light receiver 18, the thresholds may be provided to multiple inspection machines thereby avoiding the need to set thresholds for each machine individually. This reduces downtime between job changes, facilitates setting up multiple inspection machines, and improves repeatability and reliability of the inspection results. The thresholds can also be adjusted by an inspection machine operator, if desired. This may help accommodate some misalignment or variations in placement of the light receiver 18 relative to the containers 12 being inspected from one machine to another, or from one inspection cycle to another.

Further, because ambient light may vary from one inspection machine to another, or over time, it may be desirable to filter the ambient light level out of the signals generated by the light sensors 24 so that ambient light readings do not affect the comparison of reflected or refracted light to the thresholds. To filter out ambient light detected by the sensors 24, a light reading for all sensors 24 may be taken when no light source is energized and the sensors are activated. In processing the signals, the ambient light level can be removed from reflected and/or refracted light signals for a more accurate comparison of container light reflections or refractions to the threshold. Of course, other methods to filter out ambient light levels can be used, including more complicated methods that account for the high-speed ambient strobe lights.

As a container 12 is rotated for inspection, the light sources 14, 16 are individually energized in sequence, and the intensity of light detected by the sensors 24 (including that caused by light reflected or refracted into the light source by commercial variations) in response to the output from each light source is recorded and processed by the processor 20. In one implementation, the intensity of light detected by the individual sensors 24 in a channel may be added together to obtain one signal per channel. If a signal from a channel shows a light intensity detected by the channel that is greater than the threshold set for that channel, a signal may be sent by the processor 20 to reject the container 12 for presence of an unacceptable commercial variation, such as a check, in the container neck finish 22.

The signal for each channel may be compared to signals from one or more earlier inspections. In one form, the signal for a channel may be compared to or subtracted from one or more earlier signals for that channel from one or more prior inspections. This can be done before comparison to the threshold for that channel. The sampled data can be performed digitally and may be done at a constant number of points as the container rotates, such as, for example, 500 points per container rotation. This may be accomplished with a shaft encoder on the inspection machine material handler. As the material handler rotates the container faster, the shaft encoder signals will be closer in time and the signal samples will be taken faster, and vice versa. The end result is that the container rotation between samples is constant even though the rotational speed of the container may vary. Therefore, the distance on the container determined from a given number of samples will be constant even as the rotational speed of the container varies.

Further, information from the sensors 24 can be used to discriminate between different types of commercial variations. For example, a blister or bubble will tend to reflect light in all directions from all light sources 14, 16 that illuminate it. Therefore, light reflected off the container from all light sources 14, 16 can be analyzed to distinguish or discriminate a blister or bubble from a check. Example techniques to discriminate between different types of commercial variations will be discussed below.

The light reflected from the container 12 may be collected and analyzed in a spatial domain and/or in an angular domain. The terminology spatial domain and frequency domain are commonly used in the optical engineering field, and there are transforms that can transform image data from one domain to the other domain, like the Fourier Transform. But there is no such transform to convert image data between the spatial and angular domains. The information used to generate an image in the angular domain is not in the spatial domain. Instead, the angular domain image is created directly from the object being imaged, by using an optical method that is different from the optical method that is used to create the spatial domain image. Accordingly, an image produced in the angular domain is a totally different type of image with different information in the image, in contrast to an image obtained in the spatial domain.

Figure 6A:
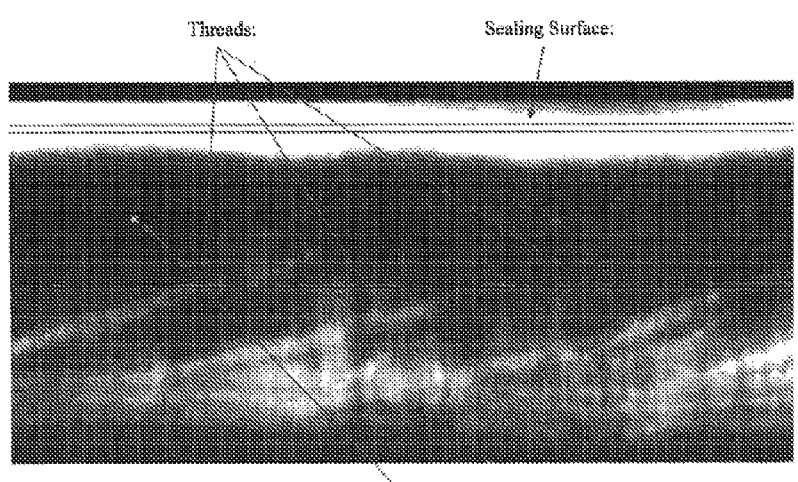
FIG. 6A is a two-dimensional image of a portion of a container neck finish, obtained in a spatial domain using the apparatus of FIG. 1.

FIG. 6A illustrates an example of an image produced in a spatial domain and representing a circumferential portion of a container neck finish with a possible commercial variation C. The horizontal axis of the image may represent the circumferential dimension of the neck finish over the time the container is moved. Accordingly, the circumferential portion of the finish appears "unwrapped" and displayed as a flat two dimensional image obtained from the light source scan and from the information received from the sensor groups using a suitable processor or computer. A sealing surface of the finish can be seen as a bright band in the top of the image. Diagonal threads can be seen faintly in the center of the image. Also, a bright spot in the image indicates the commercial variation C. But in the spatial domain image it is not always possible to reliably determine whether the commercial variation is a blister or a check.

The image was obtained with a line scan camera as the container rotated. Each point in the two dimensional image could be created by summing all of the image sensor cells at each instance in the light source line or scan. The vertical axis of the image may be produced from the light source scan, wherein a sum of the light signals may be from any desired number of sensor groups.

Also, portions or zones within the image can be created for a region of interest in the neck finish. Each zone could create or form an inspection channel that can be analyzed by a suitable processor or computer. Multiple zones could be used without additional light sources or masks. The zones could also be dynamically created. For example, as shown at the top of the image, light reflected or refracted from a sealing surface of the container could be detected and the zone started dynamically from this point to minimize or eliminate this sealing surface light from detection or at least being analyzed with other reflections and refractions.

Figure 7A:
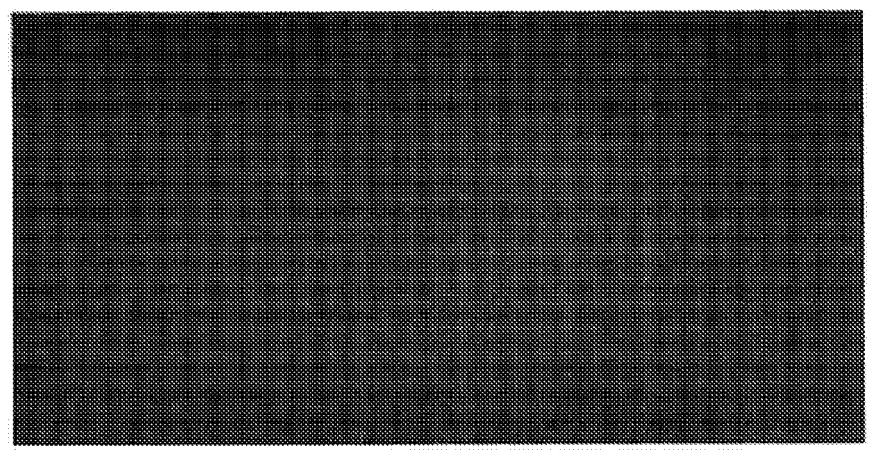
FIG. 7A is a two-dimensional image of a portion of a container neck finish, obtained in an angular domain using the apparatus of FIG. 1.

FIG. 7A illustrates an example of an angular domain image of a comparatively discrete portion of a container neck finish.

For example, the image in FIG. 7A could correspond to the relatively point-sized commercial variation C in FIG. 6A. Each point in the angular domain image represents, at one instant during the light source scan, the signal of a particular image sensor portion or cell of the light receiver wherein the light receiver is flattened onto a rectangular image format. Accordingly, the method may result in thousands of images similar to the image in FIG. 7A. The image of FIG. 7A has upper and lower margins that are generally very dark, and a horizontal band that is lighter than the margins with a large lighter portion just right of center.

Individual rays of light reflected from the container extend at unique or different angles that correspond to unique or different light sensors or different portions of the plurality of light sensors, and commercial variations in the container can be identified by analyzing reflection angle and intensity of the reflected light received by the plurality of light sensors. For example, the image in FIG. 7A is illustrative of a commercial variation that reflects light according to a relatively larger set of angles on the right side of the image and a relatively smaller set of angles on the left side of the image. The pattern of light reflected from that commercial variation and captured in the angular domain image can be analyzed in determining whether a commercial variation is a check, a blister, or something else. The determination may be facilitated by imaging software with pattern recognition functionality, or by any other suitable software and/or techniques as will be described in more detail herein below.

Figure 6B:
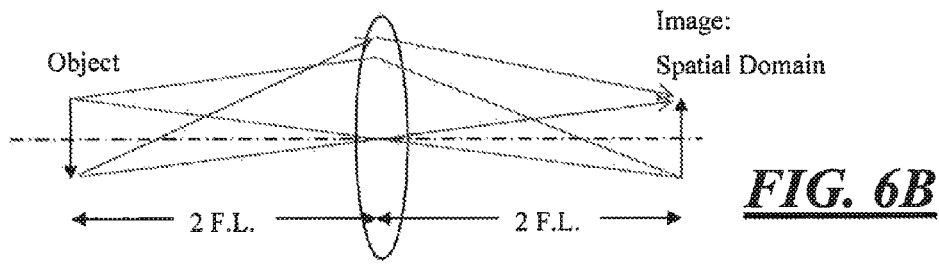
FIG. 6B is a schematic view of an object, a lens, and an image in a spatial domain image plane according to a spatial domain configuration.

With reference to FIG. 6B, for an image in the spatial domain, all light rays reflected off a common point or portion on an object travel through a lens for imaging to a corresponding common point of an image of the object, and different points on the object are imaged to corresponding different points of the image in the spatial domain image plane. In other words, imaging in the spatial domain involves point to point correspondence between the object and the image, independent of light ray reflection angle. The distances from the lens shown in FIG. 6B gives a magnification of 1. The general formula to create a spatial domain image is $$\frac{1}{f} = \frac{1}{o} + \frac{1}{i}$$

where f is the focal length (FL) of the lens used between the object and the image, o is the object distance, and i is the image distance. The magnification is given by $$m = \frac{i}{o}$$

If i and o are equal as in the drawing figure, then i and o are equal to 2*f (2 FL in the drawing figure) and the magnification is 1.

Figure 7B:
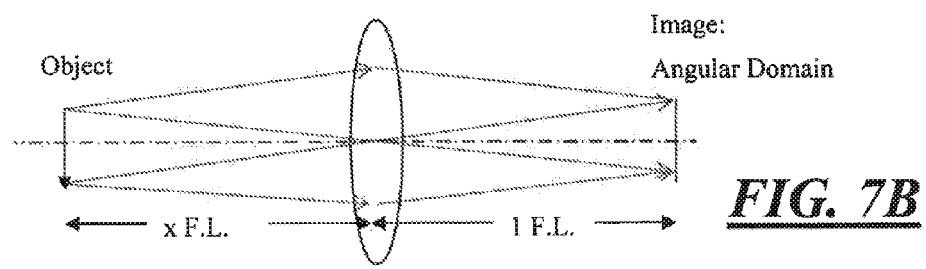
FIG. 7B is a schematic view of an object, lens, and image according to an angular domain configuration.

In contrast to FIG. 6B, and with reference to FIG. 7B, for an image in the angular domain, all parallel light rays reflected off a common portion of an object travel through a lens for imaging to a common point on the image. The location of this point is determined by the angle of the parallel rays. Parallel rays reflected off another common portion of the object at a different angle will be imaged to a different point in the image. Conversely, non-parallel rays reflected off a common point or portion of the object are imaged to different points in the image. In other words, imaging in the angular domain involves angle to point correspondence between the object and the image, dependent on light ray reflection angle. Angular domain data is representative of reflection or refraction characteristics of a region in a container being illuminated by the light source. This method is referred to as the One FL Lens method and produces an "image" in the sense that that light patterns are captured by the light sensors. However the angular domain image is not an "image" in the normal sense of an image of an object. Accordingly, the terminology "angular domain image" may include a light pattern and corresponding electronic signals or data.

Therefore, the present disclosure includes a method for detecting commercial variations in at least a portion of an at least partially transparent container. The method includes directing light toward a region of interest of the container from at least one light source such that the directed light reflects off the region of interest as reflected light rays extending at different reflection angles. The method also includes receiving the reflected light rays with a plurality of light sensors, wherein parallel ones of the reflected light rays travel to common portions of the light sensors and non-parallel ones of the reflected light rays travel to different portions of the light sensors. The common portions of the light sensors may include, for example, individual light sensors of a plurality of light sensors or individual cells of an individual light sensor of the plurality of light sensors. The method further includes establishing a light pattern in an angular domain from signals generated by the light sensors, wherein each point in the light pattern is generated by a signal from a corresponding portion of the light sensors and represents a light intensity corresponding to a particular reflection angle. The method additionally includes differentiating between different types of commercial variations in the container by analyzing the light pattern in the angular domain.

The method also may include separating acceptable containers from reject containers, which include unacceptable commercial variations identified by the method set forth above. The separated acceptable containers may be sold, packaged, shipped, and placed into commerce, whereas the reject containers may be recycled for use as cullet.

Figure 7C:
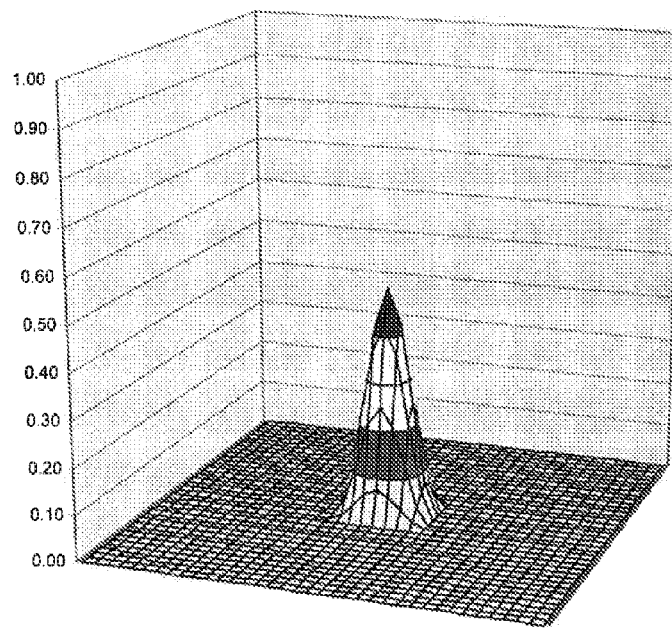
FIG. 7C is a three-dimensional plot of a check-type of commercial variation obtainable by an angular domain configuration.
Figure 7D:
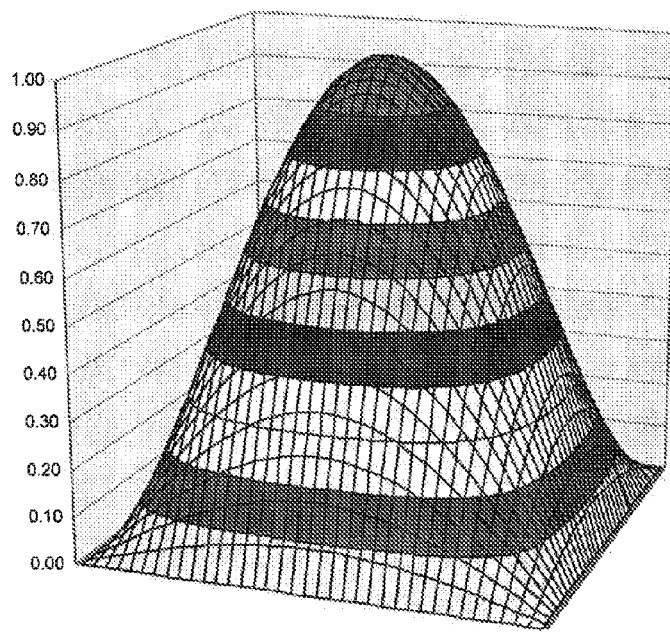
FIG. 7D is a three-dimensional plot of a blister-type of commercial variation obtainable by an angular domain configuration.
Figure 7E:
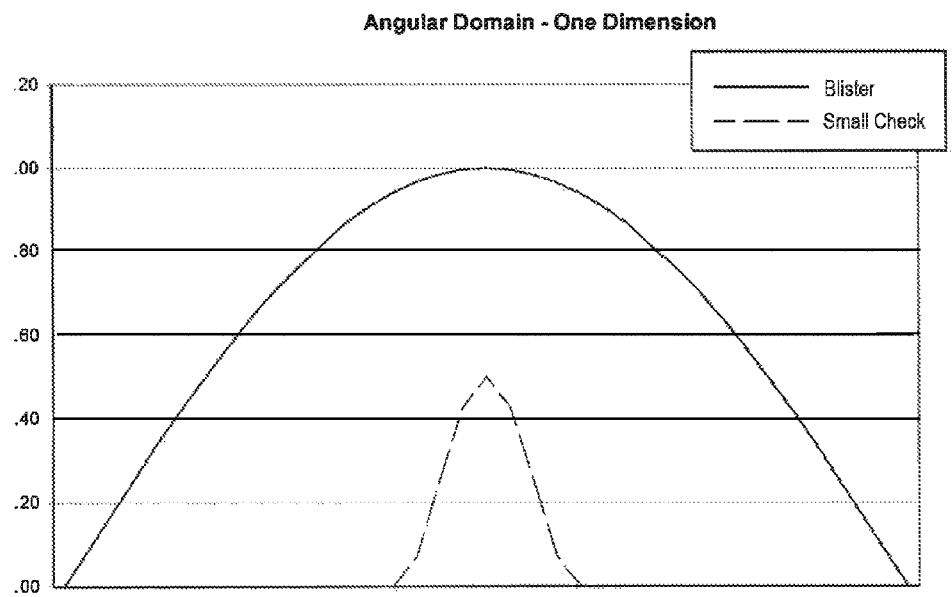
FIG. 7E is two-dimensional plot of the check of FIG. 7C and the blister of FIG. 7D.
Figure 7F:
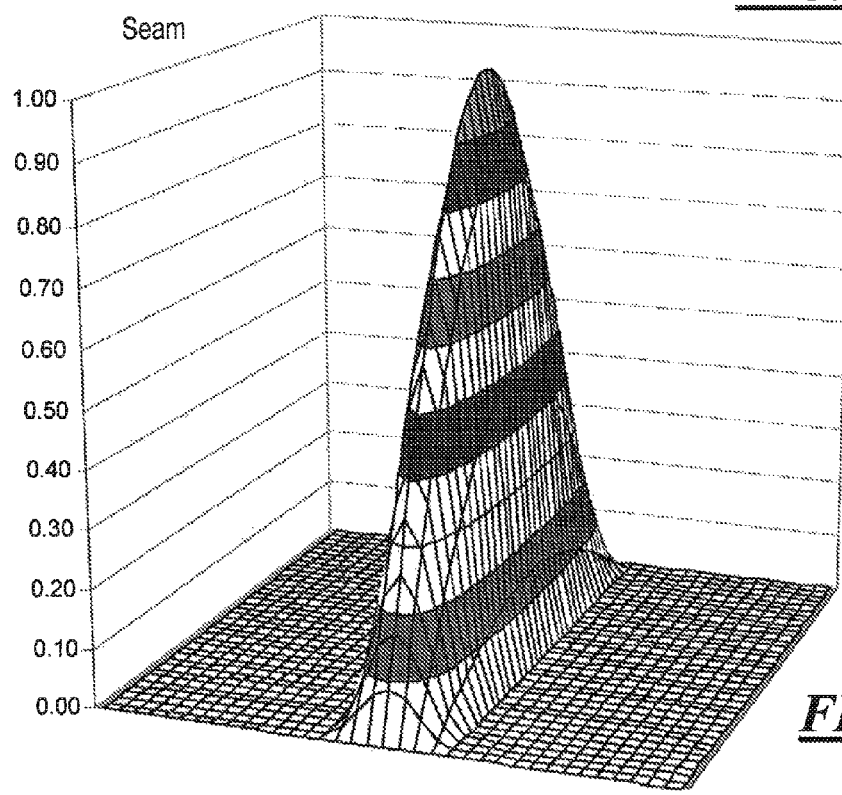
FIG. 7F is a three-dimensional plot of a container seam obtainable by an angular domain configuration.

FIGS. 7C-7F illustrate angular domain images for various commercial variations according to theoretically perfect situations. But images from actual conditions would vary from these theoretical conditions. As shown in FIG. 7C, a small check would act like a flat mirror and would reflect light from the light source in a singular direction. The check would appear in the angular domain image as a sharp spike. The location of this spike in the angular domain image would be dependent upon the angle of the reflective surface of the check. As shown in FIG. 7D, a blister would act like a spherical mirror and would reflect light in many different directions. The corresponding image would be a slowly changing level over much of the angular domain data. As shown in FIG. 7E, the small check of FIG. 7C and the blister of FIG. 7D can be represented in a two-dimensional graph. As shown in FIG. 7F, a vertical seam in the container neck finish would effectively "smear" the laser beam horizontally, such that the angular domain data would tend to extend more horizontally.

It is interesting to note that either the small check or the blister could produce the bright spot in the spatial domain image of FIG. 6A. It is also interesting to note that use of a mere threshold level during inspection would not be effective to reject the check but allow the blister to pass in the spatial domain: both the check and the blister would be rejected.

Accordingly, pattern recognition software and/or techniques in the angular domain can be used to reject the small check and pass the much larger blister. For example, the following algorithm may be used to qualify and quantify a commercial variation to facilitate differentiation between different types of detected commercial variations.

Find a peak value associated with a detected commercial variation, for example, from an angular domain light pattern. The values are proportional to the total amount of light on the sensors.

Find an average width of the signal in degrees that is above 50% (or some other suitable threshold value) of the peak value in both horizontal and vertical dimensions. Since each sensor represents the light from the bottle at a particular angle and different sensors represent different angles, the location of each sensor can be calibrated into the degrees (or any other unit of arc) of the reflected light in two dimensions. If the average width is greater than some threshold value in both dimensions, then the commercial variation is determined to be a blister.

If the average width is greater than the threshold value in only the horizontal dimension, then the commercial variation is determined to be a vertical seam.

If the average width is greater than the threshold value in only the vertical dimension, then the commercial variation is determined to be a horizontal seam.

If the average width is smaller than the threshold value in both dimensions, then the commercial variation is determined to be a check.

Calculate a volume under surfaces of shapes of the commercial variations (e.g. FIGS. 7C, 7D & 7F) by summing the signals for all pixels in plots of the shapes. The calculated volume represents a severity of the determined commercial variation.

Use a separate threshold level for each type of commercial variation to determine if the particular commercial variation should be rejected. For example, a small check could be rejected, but a larger blister could be passed.

The algorithm may proceed sequentially through the above steps, or in any other suitable order.

According to the presently disclosed method, a portion of the container 12 is illuminated with a scan from a light source, for example, a laser beam scan, and an image in the angular domain is established over a very large solid angle. For instance, an angular domain image can be created for each point in a laser beam scan. The container then can be rotated and the laser would go through one complete scan for each increment of rotation. The laser beam may be scanned vertically if desired to cover a larger region on the container. Alternate configurations could be made where the container would move linearly through inspection, rather than rotating. Either method of container handling could be used, although discussion herein generally includes container rotation.

Light collected in the angular domain can be converted to electrical signals by multiple methods. One method may include placing a CCD or CMOS sensor at the angular domain image plane. But the high resolution obtained by such sensors is not required to produce an acceptable image in the angular domain, and the frame rate required for such sensors is very high. An alternate method includes placing a discrete sensor cell array at the angular domain image plane. The discrete sensor cell array may include 8 cells by 8 cells for a total of 64 cells, and signals from the 64 cells may be amplified in parallel, converted to digital signals with an A/D converter, serialized, and sent to the processor 20 for analysis. The cells may be carried by a dome, for example, the dome 17 of FIG. 5, or any other suitable apparatus.

The angular domain imaging method differs from other methods that detect rays of light emanating from an object at multiple different angles. With angular domain imaging, each angle represents one point or pixel in the angular domain image. Other commercial check detection systems detect light from multiple angles, but there are two basic differences between those methods and the presently disclosed method. First, other systems produce spatial domain images of one or more pixels (typically 10 to 20 pixels) from light detected at multiple angles, but those systems detect the mere presence of light corresponding to each of those angles. In contrast, the presently disclosed method involves detecting a pattern in an angular domain image, and not just the mere presence of light corresponding to angles. Second, and similarly, other systems may detect light at 10 to 20 angles, but primarily indicate where light is absent or present but would not show patterns of light intensity or degree. Third, other systems process only individual points and not patterns. In contrast, the presently disclosed method may include using an imaging sensor array with a minimum resolution of 6×6 or a total of 36 pixels. It is believed that analysis of patterns in the angular domain will increase the reject rate of real checks and reduce false rejects.

A single point in a spatial domain image may be established by summing data from either an entire angular domain image or a portion of the image. Additional points, vertically, would be obtained in a similar manner as the laser is scanned vertically. Additional points, horizontally, would be obtained as the container rotates. Accordingly, each point in the two-dimensional image in the spatial domain image plane may be represented by another two-dimensional image in the angular domain. In other words, an angular domain image corresponds to a singular point in a spatial domain image.

The multiple panels of the light receiver capture the reflections from the container. From each panel, an angular domain image is established either by the One FL Lens method or the Direct method. For the Direct method, the panel may include a sensor cell array. For the One FL Lens method, the panel may include a lens and sensor cell array.

Figure 7G:
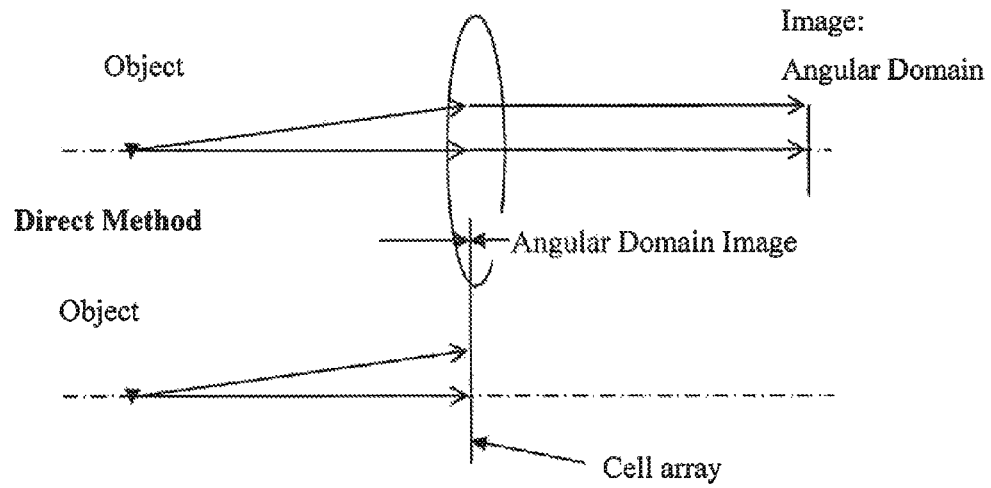
FIG. 7G is a schematic view of a small object, lens, and image according to a One FL Lens configuration to produce images in an angular domain, and of a small object and sensor cell array according to a Direct configuration to produce images in an angular domain.

With reference to FIG. 7G, angular domain images may be captured even if the size of the object to be imaged is very small. As shown at the top of FIG. 7G, an angular domain lens can be used to capture light rays emanating from a small object to be imaged as an angular domain image according to the One FL Lens method. In contrast, as shown at the bottom of FIG. 7G, the lens can be omitted and replaced with a sensor cell array in its place, according to the Direct method. If the object is small and is on the object plane, then an image captured by the sensor cell array would be the same as an angular domain image established by the One FL Lens method.

Figure 7H:
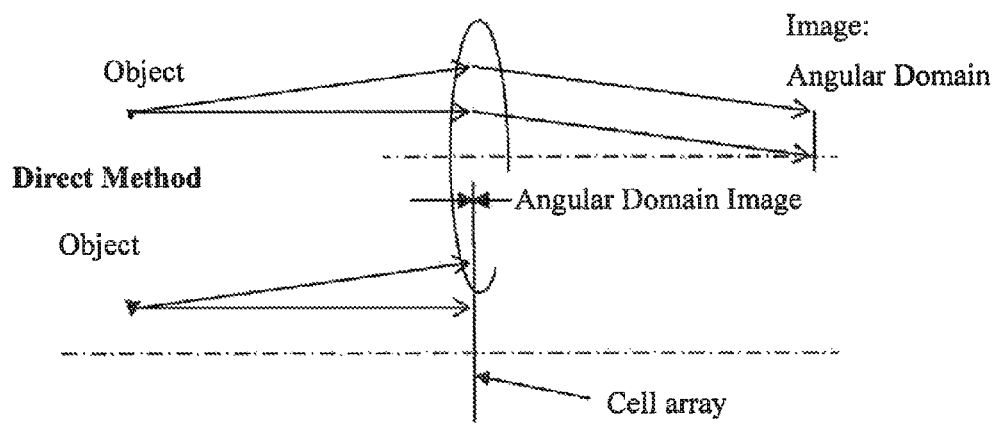
FIG. 7H is a schematic view of a shifted small object, lens, and image according to a One FL Lens configuration to produce images in an angular domain, and of a shifted small object and sensor cell array according to a Direct configuration to produce images in an angular domain.

Referring now to FIG. 7H, if the location of the object changes, for example, away from the optical axis, the Direct method still can be used. As shown at the top of FIG. 7H, the angular domain lens is used to capture rays of light emanating from the shifted object. In contrast, as shown at the bottom of FIG. 7H, the lens has been omitted and replaced with the sensor cell array in its place, wherein the image of the object is shifted by the amount that the object was shifted relative to the optical axis.

If a vertical location on the container is from a light source scan, then at any point in time during the scan, the "object" size will be small and the corresponding vertical location of the "object" will be known from the light source apparatus, such that the angular domain image from the Direct method can be corrected for the shift shown above. For example, if a single angular domain image is desired for the object in FIGS. 7G and 7H, then the angular domain image in FIG. 7H could be shifted downwardly by the amount of the shift of the object between FIGS. 7G and 7H and added to the image of FIG. 7G. If the angular domain image is desired over, for instance, 100 points in a vertical scan, then this process would be repeated 100 times for the scan. Each image would be shifted by the amount of the laser scan and then all 100 images would be added.

Both the One FL Lens method and the Direct method are very viable implementations for the light receiver. The One FL Lens method involves a more accurate implementation of a mask, but may involve a much larger device to accommodate the lenses and, thus, might not fit on some inspection machines, and also may have some degraded performance from scatter from Fresnel lenses.

Figure 7I:
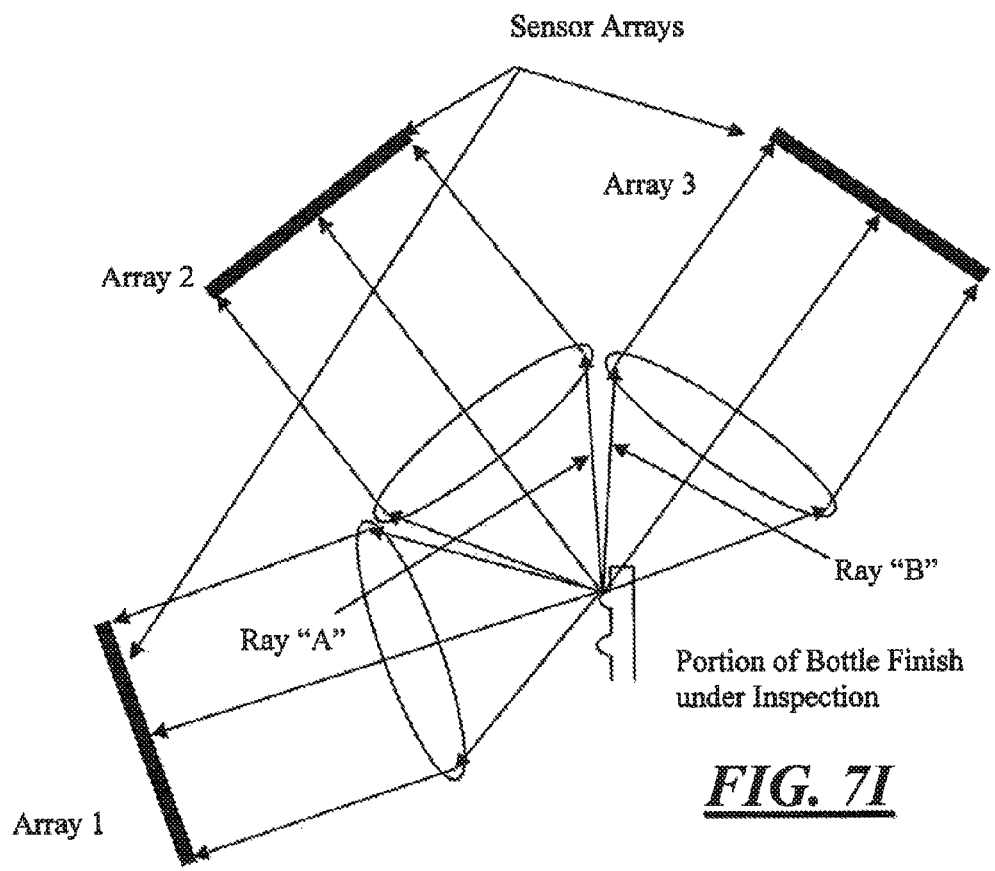
FIG. 7I is a schematic view of a container neck finish, lenses, and sensor arrays according to a One FL Lens configuration to produce images in an angular domain.

For example, with reference to FIG. 7I, several sensor arrays and corresponding lenses are illustrated in relation to a portion of a container neck finish. The sensor arrays and lenses may be part of a light receiver and carried by a dome in any suitable manner. Fresnel lenses could be used for the lenses in the 1 FL Lens Method. The Fresnel lenses could be cut to the desired size. The array would be a similar in size and shape to the lens. Each sensor array above would be in the same shape as the lens and could contain 50 to 100 individual cells.

Figure 7J:
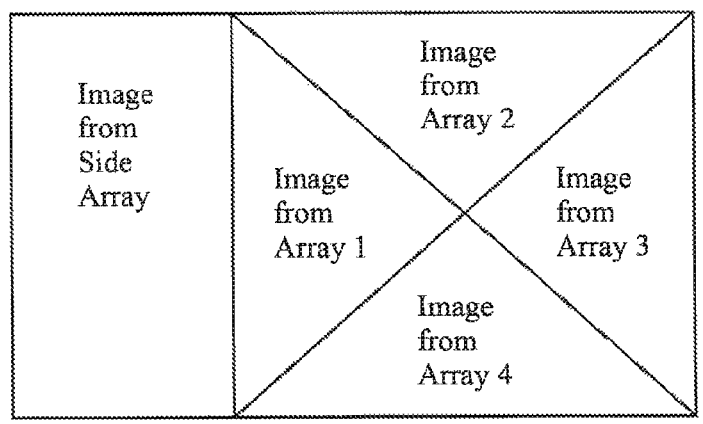
FIG. 7J is a schematic view of an image produced from a light receiver having side array and four triangular arrays.

As shown in FIG. 7I, rays "A" and "B" emanating from a container neck finish have angles that are very close to each other, but ultimately are captured on adjacent sensor arrays. Therefore, images produced by the sensor arrays can be thought of and displayed as one large contiguous image, even though the actual sensor arrays are greatly separated in physical space. These individual images could also be combined to create a larger angular domain image. For example, if the light receiver is configured with one side array and four triangular arrays as in FIGS. 1-5, then the combined image could look like that shown in FIG. 7J. In another embodiment, according to the Direct method, each lens could be replaced by a sensor cell array. This would give virtually the same information but with a simpler implementation.

Figure 8A:
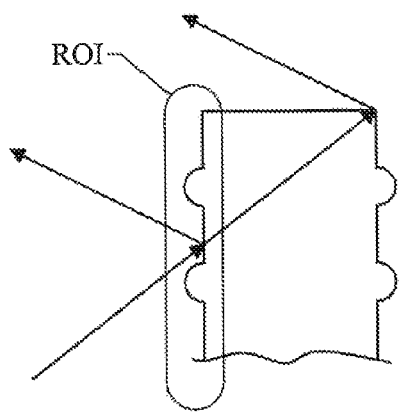
FIG. 8A is a schematic view of light reflected off a region of interest of a container neck finish and light reflected off a portion of the container neck finish that is outside the region of interest.

FIG. 8A illustrates a potential problem that may be solved in accordance with the present disclosure. Ambient light can be removed from a signal by modulation of the laser or light sources 14, 16, but light from the light sources 14, 16 that impinge on an area or region of interest (ROI) and then reflects or refracts to some other object such as the underside of the dome or the back of the container neck finish could end up on the sensor cells as extraneous light. Note that the two reflected beams in FIG. 8A have the same angle (parallel) and, therefore, would appear in the same location of an angular domain image. The beam from the ROI needs to be detected while the beam from outside the ROI (from the back of the finish in this example) needs to be blocked.

Figure 8B:
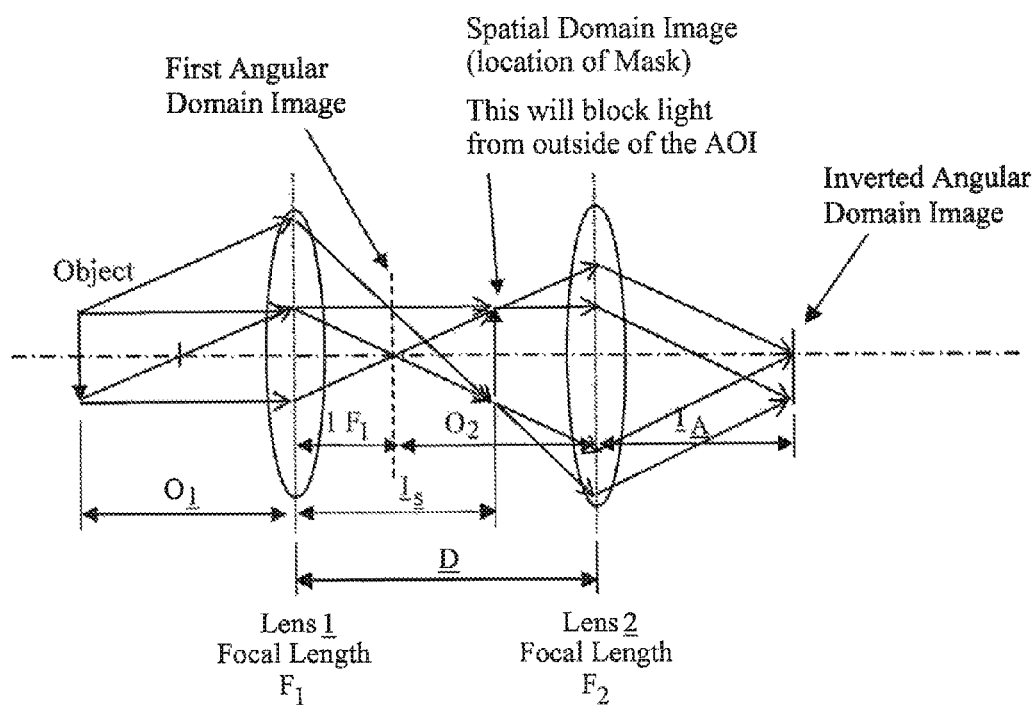
FIG. 8B is a general schematic view of a lens masking arrangement to block light reflected the portion of the container neck finish that is outside the region of interest illustrated in FIG. 8A.

With reference to FIG. 8B, a mask can be used to block undesired light. A first lens (Lens 1) produces both an angular domain image and a spatial domain image, at different distances from the first lens. A mask is located between the first and second lenses at the location of the spatial domain image produced by the first lens. For example, the mask may include an opaque thin sheet that has a clear opening therethrough whose size, shape, and location corresponds to the region of interest to allow light to pass therethrough, and that is opaque elsewhere to block light. The mask opening does not have to be extremely precise because the region illuminated by the light source will precisely control the region to be inspected. The mask just limits unwanted reflections from areas other than from the ROI. A second lens (Lens 2) is a relay lens that can reproduce the angular domain image onto a new image plane. A reproduced angular domain image is identical to the original angular domain image except that it is inverted, and the light from other than the ROI is blocked by the mask in the spatial domain image plane. In other words, an angular domain image is created using only the light from the ROI on the container, and light rays from secondary reflections are blocked by the mask. One or both of the lenses may include a Fresnel lens, or any other suitable lens. Fresnel lenses can be cut to desired size, are inexpensive, and have large angle collection capability (small f-number).

The two lenses can have different Focal Lengths, wherein the focal length of the first lens is $F_1$ and the focal length of the second lens is $F_2$. The first angular domain image will be one $F_1$ from the first lens. This is true regardless of the distance of the object from the first lens, wherein that distance is $O_1$, which can be any value greater than $F_1$. The distance from the first lens to the spatial domain image is $I_S$, which can be calculated using the standard lens equation as follows, wherein f is the lens focal length, o is the object distance and i is the image distance:

$$\frac{1}{f} = \frac{1}{i} + \frac{1}{o}$$

Using $f=F_1$, $i=I_S$, and $o=O_1$ and solving for $I_S$ gives the following equation:

$$I_S = \left(\frac{1}{F_1} - \frac{1}{O_1}\right)^{-1}$$

The magnification ($M_S$) of the spatial image is given by standard lens equation as follows:

$$M_S = \frac{I_S}{O_1}$$

Note that the spatial domain image can be made the same size as the object ($M_S=1$) if $I_S=O_1=2F_1$.

The distance from the first angular domain image to the second lens is $O_2$ and the distance from the second lens to the second angular domain image $I_A$. $O_2$ can be any distance that is both greater than the focal length of the second lens $F_2$ and greater than $I_S-F_1$. $I_A$ can now be calculated by the same lens formula as follows:

$$I_A = \left(\frac{1}{F_2} - \frac{1}{O_2}\right)^{-1}$$

The magnification ($M_2$) of the second angular domain image uses the same standard lens magnification formula as follows:

$$M_A = \frac{I_A}{O_2}$$

Note that the second angular domain image can be made the same size as the first angular domain image ($M_A=1$) if $I_A=O_2=2F_2$.

The distance between the lenses can be defined as D, as follows:

$$D=F_1+O_2$$

From these equations, the locations of the primary elements can be derived in terms of the lens focal lengths and the magnification of the spatial image from the first lens ($M_S$) and the magnification of the angular domain image from the second lens $M_A$. The distance $I_S$ in the distance from the first lens to the mask (location of the spatial image).

$$O_1 = \left(\frac{M_S+1}{M_S}\right)F_1$$

$$I_S = (M_S+1)F_1$$

$$D = F_1 + \left(\frac{M_A+1}{M_A}\right)F_2$$

$$I_A = (M_A+1)F_2$$

Figure 8C:
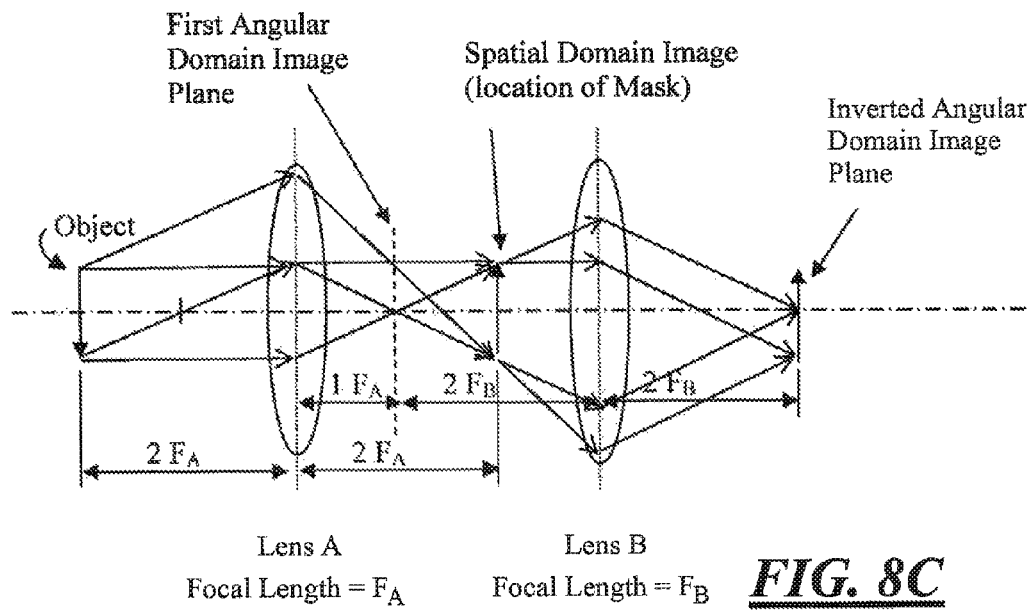
FIG. 8C is a specific schematic view of a lens masking arrangement to block light reflected the portion of the container neck finish that is outside the region of interest illustrated in FIG. 8A.

FIG. 8C represents a specific example, wherein the distance from the object to a first lens (lens A) can be twice the focal length of the first lens, wherein an angular domain image is created at one focal length from the first lens A and a spatial domain image is created from the first lens at twice the focal length from the first.

Figure 8D:
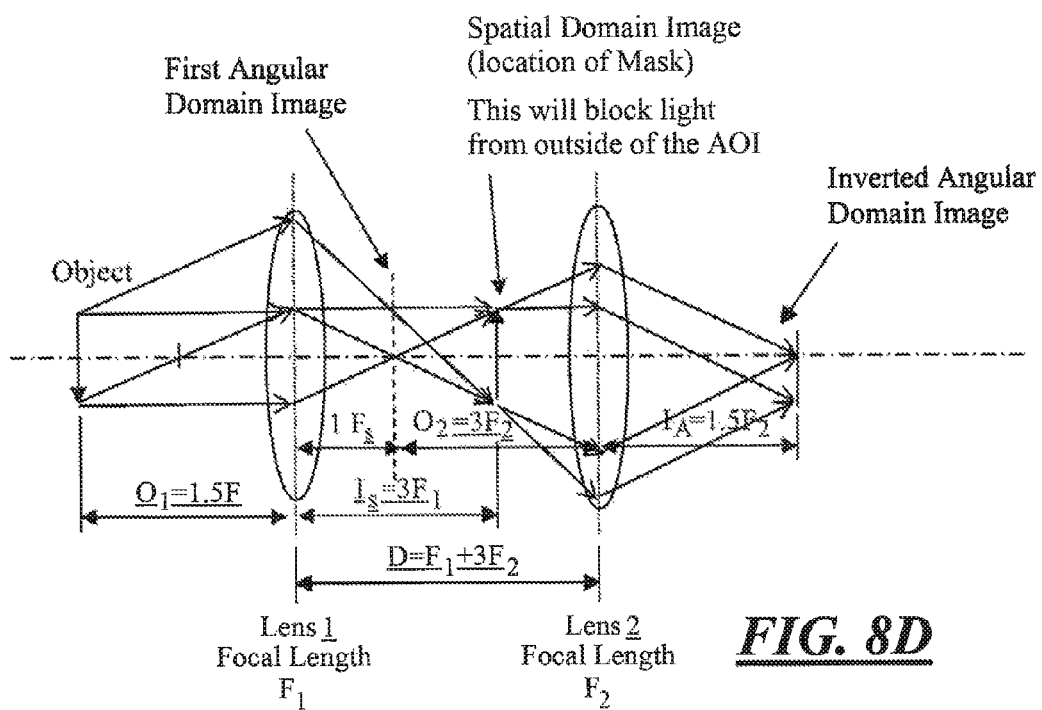
FIG. 8D is another specific schematic view of a lens masking arrangement to block light reflected the portion of the container neck finish that is outside the region of interest illustrated in FIG. 8A.
Figure 8E:
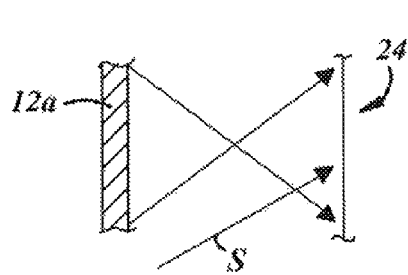
FIG. 8E is a schematic view of a portion of a light sensor and container, illustrating stray light incident upon the light sensor.

FIG. 8D represents another specific example, with a magnification of two to create a spatial domain image twice the size of the object. This will allow for a larger, more precise mask to be used. The second lens has a magnification of 0.5 to create the second angular domain image as half the size of the first angular domain image. This will allow for a smaller sensor array to be used.

Assume:

$$M_S = \frac{I_S}{O_1} = 2 \text{ and } M_A = \frac{I_A}{O_2} = 0.5$$

$$O_1 = 1.5F_1$$

$$I_S = 3F_1$$

$$D = F_1 + 3F_2$$

$$I_A = 1.5F_2$$

With reference to FIG. 5E, stray light reflected or refracted from the container 12 may impinge on the light sensors 24. In this regard, whereas ambient light can be removed from signals from the image sensors, such stray light may be more difficult to remove. More specifically, light from the light source or laser may hit a region of interest on the container, then reflect or refract off as stray light to some other object such as the underside of the dome or the back of the container neck finish, and then impinge on the image sensor cells as noise along with the check signals.

In the Direct method, to eliminate or reduce such stray light or noise, collimators or collimating lenses may be added in front of the image sensor cells or cell groups to limit light impinging on the image sensors to light emanating only from the region of interest on the container. Accordingly, light from a region of interest from the container would extend through a respective collimator and impinge on a corresponding image sensor cell. This may limit the light received by a sensor or group of sensors from only a desired portion of the container (e.g. a region of interest of the container) being inspected, or may limit or prevent light reflected toward the light source from other regions or sources that might otherwise be incident on the sensors along with light reflected or refracted from, for example, a check. A sensor or group of sensors with a lens or collimator could still generate the same or similar information regarding the pattern and intensity of light incident upon the sensor(s). The collimators may be of any suitable shape and arrangement. As used herein, the term "collimator" includes collimating lenses and collimators.

Figure 8G:
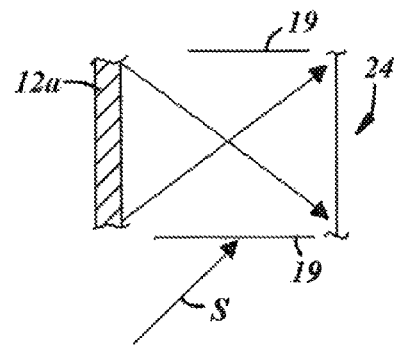
FIG. 8G is a schematic view of a portion of a light sensor and container with a collimator disposed therebetween to prevent stray light from impinging on the light sensor.
Figure 8F:
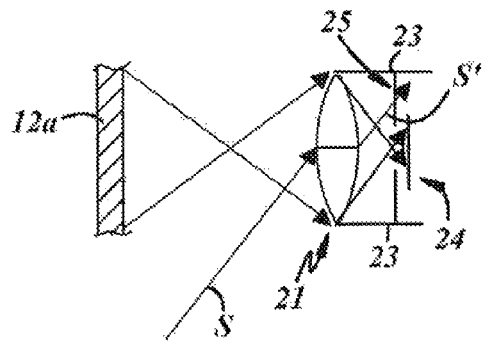
FIG. 8F is a schematic view of a portion of a light sensor and container with a collimating lens and tube disposed therebetween to prevent stray light from impinging on the light sensor.

As shown in FIG. 8F, a type of micro-lens and a tube could be used to approximate this same function. These lenses or collimators may not be necessary for implementing the presently disclosed check detection method on regions other than the container finish such as on the container sidewall. More specifically, a collimating lens 21 and corresponding tube 23 may be disposed between the region of interest 12a of a container and the image sensor 24 (or a portion thereof). The lens 21 redirects stray light S away from the sensor 24 and the tube 23 blocks such redirected stray light S' from impinging on any adjacent sensors or adjacent portions of the sensor 24. As shown in FIG. 8F, a type of micro-lens may be placed in front of each cell or pixel receiving light for the angular domain image and a mask 25 may be placed at the cell to limit the light to only from the region of interest on the container. The angular domain image would still be created. This would give the same angular domain mask limited image as obtained above with the One FL Lens Method.

Alternately, as shown in FIG. 8G, a collimator 19 may be disposed between a region of interest 12a of a container and an image sensor 24 (or a portion thereof). The collimator 19 blocks stray light S from impinging on the sensor 24. However the length of the collimator 19 must be limited such that it does not limit the light from the ROI to other adjacent sensors.

In the primary implementation of the dome, there are 5 facets with 16 cells on each polygon. Therefore 80 lenses would be required which might not be reasonable to include in a production device. And in other implementations, there may be eight boards or polygons for a light receiver, with 16 image sensor cells or cell groups on each polygon, thereby requiring 128 separate collimators.

But a cost-effective custom molded plastic lens array could be placed in front of the polygon with the cells. Each lens could have a diameter of about 0.75" and an f/1 lens would put the lens about 1" from the polygon so the full dome would grow in radius by about this 1". In embodiments where there are multiple cells in sensor groups, such multiple cells may be replaced with each collimator lens and one image sensor cell. The image of the container would be placed on this cell so the shape of the cell would determine the region of interest on the container from where light is received.

But the collimators may not form a precise image. The precise region of interest of the container to be inspected would be controlled by the light source which may be 1" vertically by 0.020" horizontally. The cell shape could be such to receive light from a region on the container of about 3/16" by 1.25". If these lenses are used, some structure such as a cylinder may be placed between the lens array and the sensor cell array board to prevent light at a steep angle to the lens from going through one lens and impinging on a different cell. Therefore each array would have 16 lenses on one piece of plastic. Each lens could be circular with some dead regions between the lenses or the lenses could be square or hexagonal to illuminate the dead regions. The lenses could be standard lenses or they could be Fresnel lenses.

Figure 8H:
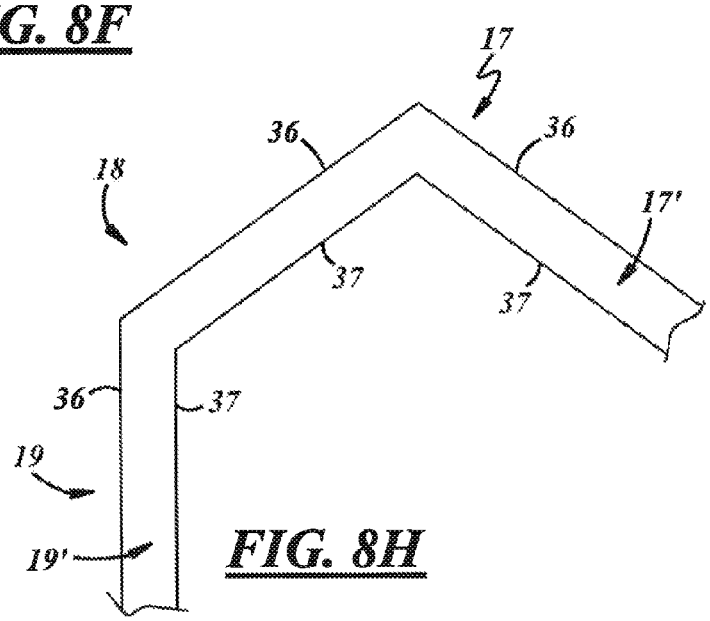
FIG. 8H is a schematic view of a light receiver and collimator which may be used in the apparatus of FIG. 1.

In a specific example as shown in FIG. 8H, collimator arrays 37 may be provided and disposed in front of each polygon of the dome 17 and the extension 19 of the light receiver 18. The collimator arrays 37 may be custom-molded plastic components and may have one collimator per corresponding cell group of the light receiver 18. Therefore, each array 37 may have 16 lenses on one piece of plastic. The collimator arrays 37 could be formed to include a dome 17' and an extension 19' that correspond to the dome 17 and extension 19 of FIG. 2. Each collimator on each array 37 could be circular with some dead regions between the collimators, or the collimators could be square or hexagonal so as to reduce or eliminate the dead regions. The collimators could include standard lenses, Fresnel lenses, or any other suitable collimating lenses.

Figure 9A:
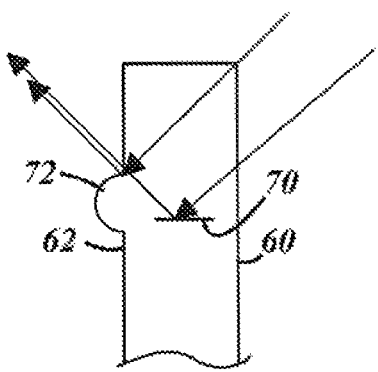
FIG. 9A is an enlarged fragmentary view of a portion of a container neck finish showing a light source directed onto an interior surface of the container neck finish and light reflections or refraction from a container thread and a check located below an upper edge of the thread.
Figure 9B:
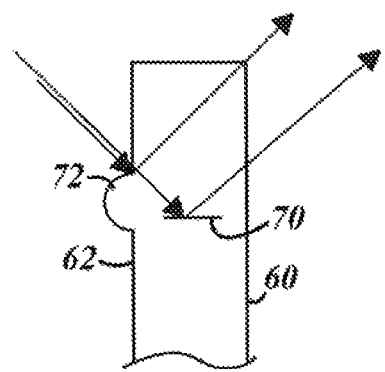
FIG. 9B is an enlarged fragmentary view of a portion of a container neck finish showing a light source directed onto an exterior surface of the container neck finish and light reflections or refraction from a container thread and a check located below an upper edge of the thread.
Figure 10A:
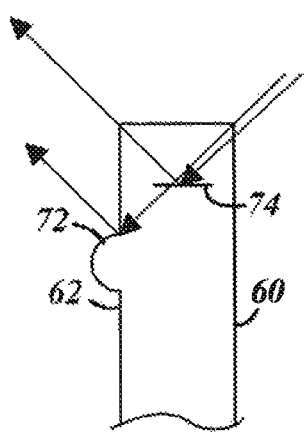
FIG. 10A is an enlarged fragmentary view of a portion of a container neck finish showing a light source directed onto an interior surface of the container neck finish and reflections of the light from a container thread and a check located above an upper edge of the thread.
Figure 10B:
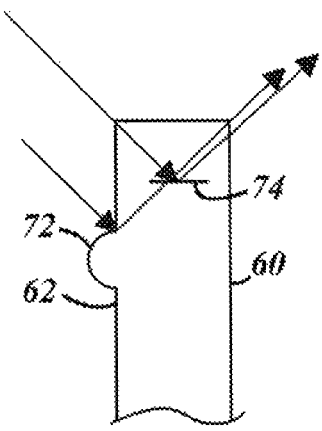
FIG. 10B is an enlarged fragmentary view of a portion of a container neck finish showing a light source directed onto an exterior surface of the container neck finish and reflections of the light from a container thread and a check located above an upper edge of the thread.

FIGS. 9A through 9B illustrate illumination of both interior and exterior surfaces 60, 62 of the container neck finish 22. FIGS. 9A and 9B illustrate an example where a check 70 is located somewhat lower than a thread 72. FIGS. 10A and 10B illustrate an example where a check 74 is located somewhat higher than the thread 72.

FIG. 9A shows that for a certain location of the check 70, light emitted onto the interior surface 60 of the container neck finish 22 and reflected off that check 70 generally may coincide with light reflected off a thread 72 on the container neck finish 22. Similarly, FIG. 9B illustrates that light emitted onto the exterior surface 62 of the container neck finish 22 and reflected off the same check 70 may be spaced apart from light emitted onto the exterior surface 62 and reflected off the thread 72.

In this latter example of FIG. 9B, although the light reflected from the check 70 and the thread 72 is spaced apart, it still may impinge on a common image sensor cell. In any event, the separation of the light rays impinging on the light sensor may not be detectable without the presently disclosed techniques.

But according to the present disclosure, it is possible to distinguish the check 70 from the thread 72. In a first example, and with reference to the interior illumination in FIG. 9A, a mask or other mechanism may be used to block the light that would otherwise be incident upon the thread 72 to prevent reflections of light from the thread 72. For instance, the previously described LCD masks 66 may be selectively activated to alternately permit and block light that would otherwise be incident upon the thread 72. Because the location of the thread 72 is known by way of set up and calibration, the LCD masks 66 may be positioned and activated to block light that would otherwise impinge on the thread 72. If no light is sensed, then it may be presumed that there are no checks present. But if light is sensed, while the thread-specific LCD mask 66 is activated, then it may be presumed that the light corresponds to the check 70.

In a second example, a scanning light source or light source may be selectively activated to scan along a region of interest including the thread 72 and the check 70. If present, the check 70 would be detected by the image sensor when the light source is aimed at the check 70 and the thread 72 would be detected separately by the image sensor when the light source is moved and is aimed at the thread 72.

FIG. 10A shows that for a certain location of the check 74, light emitted onto the interior surface 60 of the container neck finish 22 and reflected off that check 74 may be spaced apart from light emitted onto the interior surface 60 and reflected off the thread 72. But because the angles of the reflected light are identical, these features could not be distinguished in an angular domain image. Similarly, FIG. 10B shows that for a certain location of the check 74, light emitted onto the exterior surface 62 of the container neck finish 22 and reflected off the check 74 generally may coincide with light reflected off the thread 72 on the container neck finish 22. But in this case, even though the reflected light rays are coincident or at least parallel, the features can be distinguished in an angular domain image as described below.

Again, according to the present disclosure, it is possible to distinguish the check 74 from the thread 72. In a first example, and with reference to the exterior illumination in FIG. 10B, a mask or other mechanism may be used to block the light that would otherwise be incident upon the thread 72 to prevent reflections of light from the thread 72. For instance, the previously described LCD masks 66 may be selectively activated to alternately permit and block light that would otherwise be incident upon the thread 72. Because the location of the thread 72 is known by way of set up and calibration, the LCD masks 66 may be positioned and activated to block light that would otherwise impinge on the thread 72. If no light is sensed, then it may be presumed that there are no checks present. But if light is sensed, while the thread-specific LCD mask 66 is activated, then it may be presumed that the light corresponds to the check 74.

In a second example, a scanning laser or other scanning light source may be selectively activated to scan along a region of interest including the thread 72 and the check 74. If present, the check 74 would be detected by the image sensor when the light source is aimed at the check 70 and the thread 72 would be detected separately by the image sensor when the light source is moved and is aimed at the thread 72. Using this scanning light source or the LCD mask, the check could be separated from the thread in FIG. 10B but not in FIG. 10A.

Accordingly, providing illumination on both interior and exterior surfaces 60, 62 of the container neck finish 22 may lead to more reliable detection of checks and discrimination of checks from threads on the container neck finish 22.

FIGS. 11 through 15 illustrate other illustrative embodiments of apparatuses for detection of unacceptable commercial variations during inspection of a container. These embodiments are similar in many respects to the embodiments of FIGS. 1-10B, and like numerals between the embodiments generally designate like or corresponding elements throughout the several views of the drawing figures. Accordingly, the descriptions of the embodiments are incorporated into one another. Additionally, the description of the common subject matter generally may not be repeated here.

Figure 11:
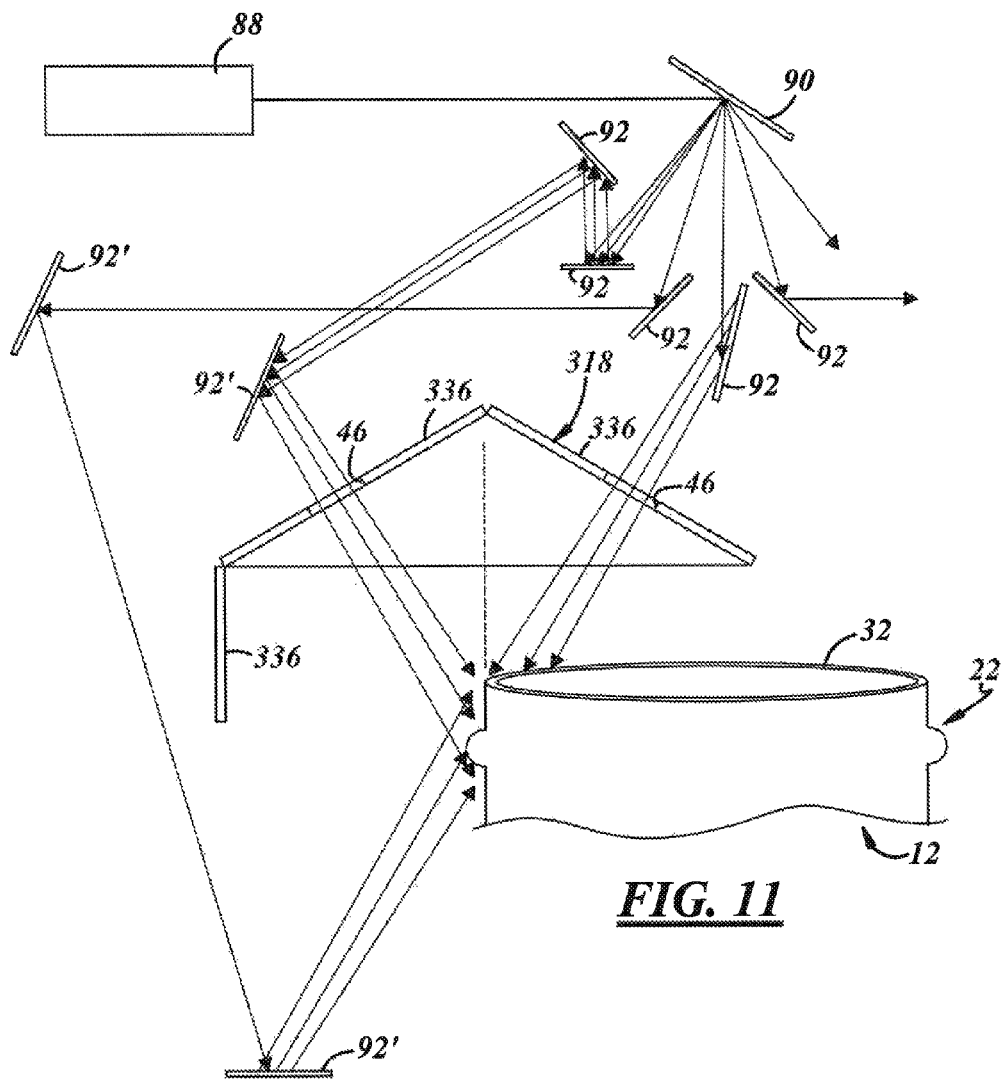
FIG. 11 is a schematic view of another embodiment of an apparatus that may be used during inspection of a container to detect commercial variations within the container.

FIG. 11 illustrates an alternate arrangement of an inspection apparatus, which may include a light receiver 318 and may use one light source 88 and one scanner (e.g. a scanning mirror 90). Here, five additional primary mirrors 92 could direct portions of the light from the scanner 90 to additional secondary mirrors 92' to the individual inspection points or lines on the container 12. One light source 88 emits light onto a scanning mirror 90 which directs light to several mirrors 92, 92' and/or onto the container 12. The light directed by the light source 88 and mirrors 92, 92' may include rays of light, beams of light, stationary lines of light, scanned lines of light, or the like.

In one form, there could be one light source, such as a laser, and one scanner (e.g. a scanning or moveable mirror) per inspection point, and there may be four inspection points as noted above. In this example, each scanner could be phase locked and the individual light sources would be enabled or activated during every fourth cycle so that only one light source would be emitting light onto the container at any one time.

In the form shown, portions of the light are directed onto mirrors and then may be directed onto the container being inspected from the same or similar directions and orientations as the first and second light sources 14, 16 of the previously discussed embodiment. For example, light may be directed through the reliefs 46 in panels 336 of the light receiver 318 and onto the container 12. Light also may be directed onto the container 12 from other directions, including for example, from a position wherein the container neck finish 22 is between the light receiver 318 and the location from which light is directed at the container 12.

Figure 12:
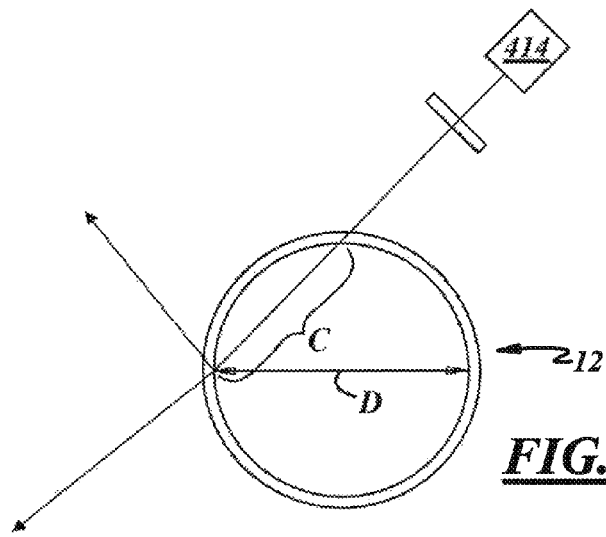
FIGS. 12 and 13 are schematic views of an additional embodiment of an apparatus that may be used during inspection of a container to detect commercial variations within the container.
Figure 13:
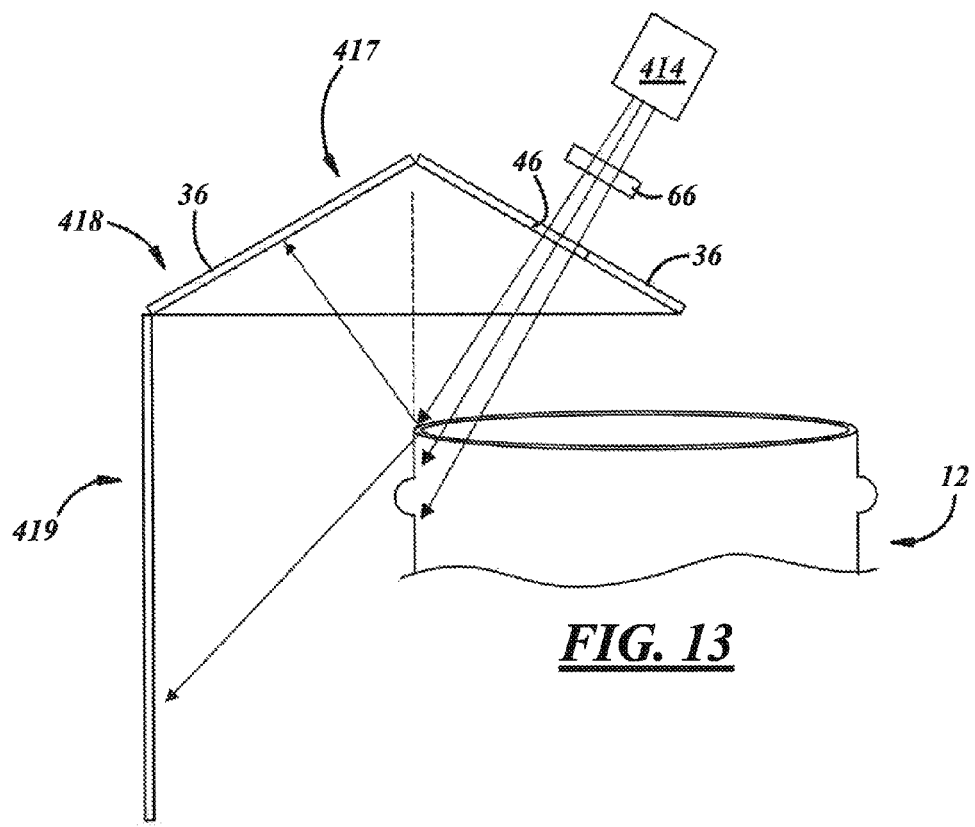

With reference to FIGS. 12 and 13, it would be possible to illuminate the container neck finish with only one light source 414 and still detect both horizontal and vertical checks. The light source 414 could illuminate the container neck finish from above, along or parallel to a chord C, rather than along or parallel to a diameter D, as embodied in FIGS. 3 and 4 for example. In other words, light from the light source 414 may be directed generally chordally across, or along the chord C of, the container neck finish 22. The reflections from horizontal checks would then reflect vertically above the container continuing on the same extension of the chord D. The reflections from vertical checks would continue on the same downward path as the illuminating light source but would be reflected off of the chord C. Accordingly, the extension 419 along the side of the container 12 may be larger to receive the reflected light from the vertical checks. Here, vertical check detection may be carried out in the opposite direction from that described with respect to FIGS. 2 and 11. This direction of the laser for detection of vertical checks could also be used in other embodiments and would reduce secondary reflections off of other portions of the finish which would reduce the need for collimator lenses, etc.

As shown in FIGS. 14 and 15, light may be directed onto different locations of the container 12 to detect checks at different locations along the container 12, such as at a container shoulder or base 79 of the neck finish 22, a container sidewall 81, a container heel 83, and/or a container bottom 85. An inspection apparatus may include additional light sources 515, 615 disposed laterally outboard of the light receiver 518. More specifically, a first additional light source 515 may be disposed laterally outboard of a dome 517 of a light receiver 518 and generally above the neck finish 22 and shoulder 79 of the container 12 to direct light onto at least one of the shoulder, or the sidewall, such that the light directed from the first additional light source 515 is reflected by commercial variations in at least one of the shoulder, or the sidewall, onto one or more of a plurality of light sensors carried by the dome 517 and/or an extension 519 of the light receiver 518. Likewise, a second additional light source 615 may be disposed laterally outboard of the extension 519 of the light receiver 518 and generally below the sidewall 81, heel 83, and/or bottom 85 of the container 12 to direct light onto at least one of the sidewall 81, heel 83, and/or bottom 85, such that the light directed from the second additional light source is reflected by commercial variations in at least one of the sidewall 81, heel 83, and/or bottom 85 onto one or more of the plurality of light sensors carried by the extension 519 of the light receiver 518.

For a scanning laser implementation, the vertical extent or travel of the laser scan may be increased to accommodate such additional container inspection. The light receiver 518 or at least certain portions of the light receiver 518 may be positioned to catch reflected or refracted light from these portions of the container 12. The additional light sources 515, 615 may be used to direct light onto the desired portion of the container 12, or a mirror or other device may be used to direct light from an already described light source onto a different portion of the container 12, as desired. The region of the container 12 illuminated can also be controlled by, for example, a scanning laser or mirror, or a mask 66. Light reflected by a check in the region of the shoulder 79 is represented by the arrow 82 in FIG. 14.

As shown in FIG. 15, a third additional light source 715 may be disposed radially outboard of the container 12 on the same side of the container 12 on which the light receiver extension 519 is located. Accordingly, light from the third additional light source 715 is directed along a chord C of the sidewall 81 of the container 12 such that light directed from the third additional light source 715 is reflected by commercial variations in the sidewall 81 onto one or more of the plurality of light sensors carried by the extension 519. The light from the third additional light source 715 may be directed in or as a vertical line.

Figure 16A:
FIG. 16a is a schematic view of a portion of a container having a vertical check.
Figure 16B:
FIG. 16b is a schematic view of a portion of a container having a horizontal check.
Figure 16C:
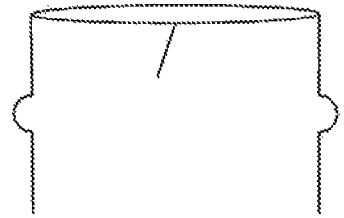
FIG. 16c is a schematic view of a portion of a container having a nearly vertical check.
Figure 16D:
FIG. 16d is a schematic view of a portion of a container having a nearly horizontal check.
Figure 16E:
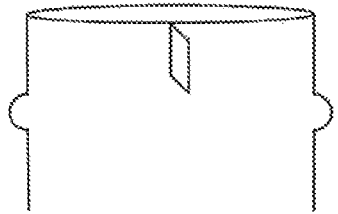
FIG. 16e is a schematic view of a portion of a container having a nearly vertical check.
Figure 16F:
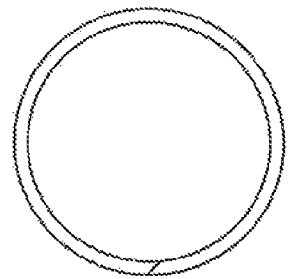
FIG. 16f is a schematic view of a portion of a container having a tilted vertical check.
Figure 16G:
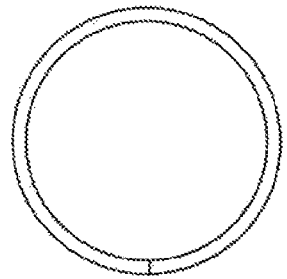
FIG. 16g is a schematic view of a portion of a container having a straight vertical check.

One or more of the embodiments described above is directed to detecting any check disposed at any angle and in any location on a container. With reference to FIGS. 16a-16g, the present disclosure addresses inspection for vertical checks, horizontal checks, any other types of checks. The primary vertical and horizontal checks are shown in FIGS. 16a, 16b as "edge on" in a view from outside the finish. Checks can also be curved in two dimensions and detected by this method, and the checks in FIGS. 16c, 16d, 16e have an angle between horizontal and vertical. The check shown in FIG. 16f is tilted as the plane of the check goes through the glass, and a horizontal check could also be tilted in a similar fashion. FIG. 16g represents a top view of a straight vertical check. The check detector may be used to detect all of the above checks with no mechanical adjustments. A simple implementation may require processing adjustments by a user to detect the checks in FIGS. 16a-16g, but with more image analysis, the pattern of the check could be detected and would not require any adjustments to detect the checks of FIGS. 16a-16g.

Also, one or more of the embodiments described above is directed to discriminating blisters distinctly from checks so that small to medium blisters can be passed if desired without changing what checks are rejected. Such discrimination may provide good feedback information for container forming process control and, likewise, check location information may provide good container forming process control feedback.

Further, one or more of the disclosed embodiments is directed to providing the light receiver as a self-contained unit where the only mechanical job change (manual or automated) may be an in/out adjustment of the entire light receiver for different finish diameters.

The present disclosure of one inspection machine to inspect a variety of containers 12 for a variety of commercial variations is in contrast to previous approaches that require, for instance, three or more separate inspection machines or stations and/or multiple adjustments at one or more stations to identify different types, locations, and/or orientations of commercial variations (e.g. one station inspecting for horizontal checks, another for vertical checks, etc.). The present disclosure enables use of one station to detect, and discriminate between, checks at various locations, curvatures, and angles wherein the checks deviate to some degree from purely horizontal, vertical, and/or radial orientations. This may be accomplished via pattern detection in an angular domain and does not require mechanical adjustments to the inspection apparatus or a separate inspection station once the apparatus is in place in the field. Also, there is no need for "check chasing" which is the adjustment of angles of light sources and sensors to detect certain angles of checks.

The disclosure has been presented in conjunction with several illustrative embodiments, and additional modifications and variations have been discussed. Other modifications and variations readily will suggest themselves to persons of ordinary skill in the art in view of the foregoing description. Further, certain relative terms have been used to, for example, discuss the relative position of certain objects such as above, below, upwardly, downwardly and the like. These terms as well as other relative terms are set forth with regard to the orientation of components and objects shown in the drawings, but could be altered in other implementations. For example, while the vertical check detecting light sources 16 have been set forth as being disposed below the container neck finish 22, if containers 12 were disposed on their side during inspection, or in some other orientation, then these light sources 16 might not be disposed below the container neck finish 22. Still further, while reliefs 46 have been shown and described in the light receiver 18 through which light may pass, the light may be reflected by a mirror carried by the light receiver so that no reliefs 46 are needed in the light receiver. In such an arrangement, the mirror may cover a portion of the surface region of the light receiver and thereby reduce the surface region about which light sensors can be arranged. In this way, the mirror may be considered the same as or equivalent to an relief in the light receiver in that a region or portion of the light receiver is still used to provide or direct light onto the container being inspected. In one scenario, a portion of the surface region of the light receiver is consumed or lost due to an relief and, in the other scenario, the surface region of the light receiver is lost due to the mirror. Of course, other possibilities and variations are possible. In another scenario, the system could be used in an inline inspection system. To do so, the light receiver could be larger, or positioned to collect light reflected or refracted from the container as the container moves. Or, the apparatus may track movement of the containers, such as by manipulating the lasers and/or mirrors to track movement of the containers being inspected. The disclosure is intended to embrace all such modifications and variations as fall within the spirit and broad scope of the appended claims.

The invention claimed is:

1. Apparatus for detecting commercial variations in at least a portion of an at least partially transparent container having an open mouth, that includes:
    at least one light source to direct light toward a region of interest of the container such that the light reflects off the region of interest as reflected light rays extending at different reflection angles;
    a plurality of light sensors to receive the reflected light rays, wherein parallel reflected light rays travel to common portions of the light sensors and non-parallel light rays travel to different portions of the light sensors, wherein the light sensors are used to establish a light pattern in an angular domain such that a point in the light pattern is generated from a signal from a corresponding portion of the light sensors and represents a light intensity corresponding to a particular reflection angle; and
    a processor to receive signals from the light sensors and differentiate between different types of commercial variations in the container by analyzing the light pattern in the angular domain.

2. The apparatus set forth in claim 1 wherein the light sensors are used to establish multiple patterns that are analyzed by the processor to identify a type of commercial variation corresponding to the multiple patterns.

3. The apparatus set forth in claim 2 wherein the type of commercial variation may be one or more of a check, blister, seam, or thread.

4. The apparatus set forth in claim 1 that includes a plurality of masks between the region of interest and the light sensors to block other light rays from impinging on the light sensors.

5. The apparatus set forth in claim 4 wherein the masks include masks in spatial domain image planes.

6. The apparatus set forth in claim 5 that includes a plurality of angular domain lenses between the light sensors and the region of interest, and a plurality of relay lenses between the light sensors and the masks, wherein the domain and relay lenses cooperate to redirect the reflected light rays so that the parallel rays travel to common light sensors of the light sensors and so that the non-parallel reflected light rays travel to the different portions of the light sensors.

7. The apparatus set forth in claim 4 wherein the masks include a plurality of collimators.

8. The apparatus set forth in claim 1 wherein said processor is responsive to an ambient light level when said at least one light source is not energized and said processor removes said ambient light level from said signals.

9. The apparatus set forth in claim 1 wherein said at least one light source directs a line of light onto the container, and said processor sums signals from said light sensors as the intensity of light detected by said light sensors to produce a two-dimensional spatial domain image having a vertical axis corresponding to each point along said directed line of light and a horizontal axis corresponding to movement of the container.

10. The apparatus set forth in claim 1 wherein the light source directs a line of light onto the container, and the angular domain light pattern is created from the signals from each sensor respectively at each point during the container rotation.

11. The apparatus set forth in claim 1 wherein at least some of said light sensors are coupled together in groups and each group provides a group signal to the processor that is representative of the intensity of light detected by that group of light sensors.

12. The apparatus set forth in claim 11 wherein said groups of light sensors are combined into a channel and the group signals from all of said groups in said channel are summed and compared to at least one threshold value to determine if an unacceptable commercial variation is detected in the container, wherein said at least one threshold value includes two different threshold values for at least two different channels.

13. The apparatus set forth in claim 1 that includes a light receiver positioned adjacent to the container and having a first side facing the container and carrying the light sensors, and a second side oppositely disposed from said first side,
wherein said at least one light source includes:
at least one first light source for directing light downwardly at an angle to said axis onto a surface of the container such that light from said at least one first light source is reflected by horizontal checks in the container onto one or more of said plurality of light sensors carried by said light receiver, and
at least one second light source disposed at a level for directing light upwardly at an angle to said axis onto a surface of the container such that light from said second light source is reflected by vertical checks in the container onto one or more of said plurality of light sensors carried by said light receiver.

14. The apparatus set forth in claim 13 wherein said at least one first light source directs light through the container mouth onto an interior surface portion of the container, and wherein said at least one second light source directs light onto an exterior surface portion of the container radially outside of said interior surface portion.

15. The apparatus set forth in claim 13 wherein said at least one first light source directs light onto an exterior surface portion of the container, and wherein said at least one second light source directs light onto the same said exterior surface portion of the container.

16. The apparatus set forth in claim 13 wherein said at least one first light source includes at least two first light sources, one of which directs light onto said exterior surface portion of the container, and the other of which directs light through the container mouth onto an interior surface portion of the container immediately inside of said exterior surface portion.

17. The apparatus set forth in claim 13 wherein either said first light source or said second light source, or both said first and said second light sources, include two light sources that direct their light energies onto adjacent or overlapping surface portions of the container.

18. The apparatus set forth in claim 13 wherein either said first light source or said second light source, or both said first and second light sources, include a mask to selectively control the intensity of light directed from said at least one light source over the associated surface portion of the container.

19. The apparatus set forth in claim 13 wherein said at least one first light source includes two light sources and the light from one of said two light sources is directed onto the container through a first relief in said light receiver, and wherein the light from another of said two light sources is directed onto the container through a second relief in said light receiver.

20. The apparatus set forth in claim 13 wherein said at least one light source also includes:
at least one additional light source to direct light onto a bottom of the container such that the light directed from said at least one additional light source is reflected by commercial variations in the bottom of the container onto one or more of said plurality of light sensors.

21. The apparatus set forth in claim 13 wherein said light receiver includes at least one depending panel extending lower than a neck finish of the container.

22. The apparatus set forth in claim 1 that includes a light receiver positioned adjacent to the container and having a first side facing the container and carrying the light sensors, and a second side oppositely disposed from said first side, wherein said light receiver is a dome having an apex that is centered above a periphery of a neck finish of the container.

23. The apparatus set forth in claim 22 further comprising collimators disposed between said light receiver and the container, wherein said collimators are integrated into molded plastic panels forming a collimator dome spaced from said light receiver dome.

24. The apparatus set forth in claim 1 that includes a light receiver positioned adjacent to the container and having a first side facing the container and carrying the light sensors, and a second side oppositely disposed from said first side, wherein said light receiver, said light sensors and said at least one light source are maintained in fixed position relative to each other and moveable as a unit relative to a container being inspected while maintaining said fixed position relative to each other.

25. The apparatus set forth in claim 1 wherein said at least one light source includes a plurality of light sources, each of which is individually energized so that at most only one light source is energized at any given time.

26. The apparatus set forth in claim 1 wherein said at least one light source directs a line-shaped light beam through at least one mask that includes an LCD having a plurality of segments which may be adjusted to vary the size of the light extending therethrough to produce the line-shaped light beam, and onto the container.

27. The apparatus set forth in claim 26, wherein said line-shaped light beam corresponds to one of a plurality of different inspection zones of the container, said different inspection zones are associated with different threshold values, and signals from said plurality of light sensors are compared to said threshold values to determine if an unacceptable commercial variation is detected in a particular zone of the container.

28. The apparatus set forth in claim 1 wherein said at least one light source includes a plurality of light sources that direct a plurality of lines of light onto the container that correspond to a plurality of different inspection zones of the container.

29. The apparatus set forth in claim 1 wherein said at least one light source directs a plurality of light beams that intersect the container along a common line.

30. The apparatus set forth in claim 1 that includes a light receiver positioned adjacent to the container and having a first side facing the container and carrying the light sensors, and a second side oppositely disposed from said first side, wherein said light receiver includes a dome, and a side extension depending downwardly from said dome, and wherein reflections from horizontal checks in the container reflect vertically above the container neck finish and impinge on said dome, and reflections from vertical checks reflect vertically below the container neck finish and impinge on said side extension.

31. The apparatus set forth in claim 1 that includes a light receiver positioned adjacent to the container and having a first side facing the container and carrying the light sensors, and a second side oppositely disposed from said first side, wherein said light receiver includes a dome, and a side extension depending downwardly from said dome, said at least one light source directs light onto a neck finish of said container such that said directed light from said at least one light source is reflected by commercial variations in the container neck finish onto one or more of said plurality of light sensors carried by at least one of said dome or said extension of said light receiver, and the apparatus further comprises at least one additional light source disposed laterally outboard of said light receiver to direct light onto at least one of a shoulder, a sidewall, a heel, or a bottom of the container such that the light directed from said at least one additional light source is reflected by commercial variations in at least one of the shoulder, the sidewall, the heel, or the bottom of the container onto one or more of said plurality of light sensors carried by said extension of said light receiver.

32. The apparatus set forth in claim 31 wherein said at least one additional light source includes a first additional light source disposed above the shoulder and the sidewall of the container, and a second additional light source disposed below the heel and the bottom of the container.

33. The apparatus set forth in claim 32 wherein said at least one additional light source includes a third additional light source disposed radially outboard of the container on the same side of the container on which said light receiver extension is located, wherein light from said third additional light source is directed along a chord of a sidewall of the container such that light directed from said third additional light source is reflected by commercial variations in the sidewall of the container onto one or more of said plurality of light sensors carried by said extension of said light receiver.

34. A method for detecting commercial variations in at least a portion of an at least partially transparent container, that includes the steps of:
    directing light toward a region of interest of the container from at least one light source such that the light reflects off the region of interest as reflected light rays extending at different reflection angles;
    receiving the reflected light rays with a plurality of light sensors, wherein parallel reflected light rays travel to common portions of the light sensors and non-parallel light rays travel to different portions of the light sensors;
    establishing a light pattern in an angular domain from signals generated by the light sensors, wherein a point in the light pattern is generated by a signal from a corresponding portion of the light sensors and represents a light intensity corresponding to a particular reflection angle; and
    differentiating between different types of commercial variations in the container by analyzing the light pattern in the angular domain.

35. The method set forth in claim 34 that includes the step of blocking other light rays from impinging on the plurality of light sensors.

36. The method set forth in claim 35 wherein the blocking step includes using a plurality of masks in spatial domain image planes.

37. The method set forth in claim 35 wherein the blocking step includes using a plurality of collimators between the region of interest and the light sensors.

38. The method set forth in claim 34 further comprising the step of monitoring said sensors to detect horizontal and vertical checks in the container as a function of the pattern of intensities of light rays reflected off the container at the different reflection angles and incident upon said sensors when said at least one light source is energized.

39. The method set forth in 38 wherein the step of monitoring said sensors includes:
    recording the light detected by said light sensors after each of said light sources is energized to direct light onto a container, wherein recording the light detected by said light sensors includes recording the intensity of the light detected by said light sensors, and
    comparing the intensity of light detected by said light sensors and comparing said intensity of light with a threshold value to determine if the detected light intensity exceeds said threshold.

40. The method set forth in claim 34 wherein said at least one light source includes first and second light sources, and further comprising the step of directing light from said second light source onto a surface of the container from a position wherein the portion of the container onto which light is directed is between said light receiver and said second light source when said first light source is not directing light onto the container such that light from said second light source is reflected by vertical checks in the container onto said light sensors carried by said light receiver.

41. The method set forth in claim 40 wherein said step of directing light from said first light source is accomplished by directing light onto an interior surface of the container neck, and said step of directing light from said second light source is accomplished by directing light onto an exterior surface of a neck finish of the container.

42. The method set forth in claim 40 wherein said step of directing light from a first light source includes directing light from a plurality of first light sources onto a container, and said step of directing light from a second light source includes directing light from a plurality of second light sources onto a container.

43. The method set forth in claim 42 wherein only one of said light sources is energized at any one time so that only one light source directs light onto a container at a time.

44. The method set forth in claim 34 wherein the processing step includes finding a peak value associated with a commercial variation, finding an average width of the signal in degrees that is above a threshold value derived from the peak value in both horizontal and vertical dimensions, and determining that the commercial variation is a check if the average width is smaller than the threshold value in both dimensions.

45. The method set forth in claim 44 wherein the processing step includes determining that the commercial variation is a blister if the average width is greater than some threshold value in both dimensions, and determining that the commercial variation is a seam if the average width is greater than the threshold value in only one of the dimensions.

46. The method set forth in claim 44 wherein the processing step also includes calculating a volume under surfaces of plots of the commercial variation by summing signals for all sensor pixels in the plots to determine a severity of the determined commercial variation.

47. A plurality of acceptable containers separated from a plurality of reject containers, which include unacceptable commercial variations identified by the method set forth in claim 34.

* * * * *